US011020542B2

(12) United States Patent
Eilat et al.

(10) Patent No.: US 11,020,542 B2
(45) Date of Patent: Jun. 1, 2021

(54) OPERATED NEBULIZER AND MEANS THEREOF

(71) Applicant: MEway Pharma Ltd., Herzliya (IL)

(72) Inventors: Eran Eilat, Herzliya (IL); Joshua Altman, Tel Aviv (IL)

(73) Assignee: Sanara Tech Ltd., Raanana (IL)

(*) Notice: Subject to any disclaimer, the term of this patent is extended or adjusted under 35 U.S.C. 154(b) by 1183 days.

(21) Appl. No.: 15/318,867

(22) PCT Filed: Jul. 3, 2014

(86) PCT No.: PCT/IL2014/050603
§ 371 (c)(1),
(2) Date: Dec. 14, 2016

(87) PCT Pub. No.: WO2015/193871
PCT Pub. Date: Dec. 23, 2015

(65) Prior Publication Data
US 2017/0128677 A1 May 11, 2017

Related U.S. Application Data

(60) Provisional application No. 62/012,474, filed on Jun. 16, 2014.

(51) Int. Cl.
*A61M 11/00* (2006.01)
*A61M 11/06* (2006.01)
(Continued)

(52) U.S. Cl.
CPC ......... *A61M 11/007* (2014.02); *A61M 11/001* (2014.02); *A61M 11/06* (2013.01);
(Continued)

(58) Field of Classification Search
CPC .. A61M 11/02; A61M 11/002; A61M 11/007; A61M 11/008; A61M 11/001; A61M 15/009; A61M 805/3028
See application file for complete search history.

(56) References Cited

U.S. PATENT DOCUMENTS 3,788,525 A 1/1974 Thornton et al.
3,856,185 A 12/1974 Riccio
(Continued)

FOREIGN PATENT DOCUMENTS

IN 8308DELNP2007 A 7/2018
WO WO9212799 8/1992
(Continued)

OTHER PUBLICATIONS

European Search Report dated Feb. 12, 2018.
(Continued)

*Primary Examiner* — Margaret M Luarca
(74) *Attorney, Agent, or Firm* — Haug Partners LLP; William S. Frommer

(57) ABSTRACT

A process and a nebulizer for dispensing a consecutively dose of medicament in the form of a mist, comprising: an energy source (ES), an air-conditioning volume, an air outlet fluidity connected to the air-containing volume, an air actuator adapted to release a flow of compressed air through the air outlet at such time as a predetermined ES pressure has been reached in the volume and at least two valve means in communication with the air actuator. The compressed air is released at a predetermined pressure of about 20 to about 100 psig. The valve means controls the actuation of the air actuator such that when a medication is nebulized, a mist distribution of a medication is formed having droplets size in the range of approximately 1μ to approximately 7μ which inhaled by a user at a set of predetermined intervals.

14 Claims, 13 Drawing Sheets

(51) Int. Cl.
  *B05B 1/02* (2006.01)
  *B05B 11/06* (2006.01)
  *B05B 7/24* (2006.01)
  *A61M 15/00* (2006.01)
  *B05B 7/28* (2006.01)
  *A61M 16/00* (2006.01)
  *A61M 16/06* (2006.01)

(52) U.S. Cl.
  CPC ...... *A61M 15/008* (2014.02); *A61M 15/0065* (2013.01); *A61M 15/0091* (2013.01); *B05B 1/02* (2013.01); *B05B 7/2421* (2013.01); *B05B 7/2424* (2013.01); *B05B 7/28* (2013.01); *B05B 11/06* (2013.01); *A61M 16/06* (2013.01); *A61M 2016/0021* (2013.01); *A61M 2016/0027* (2013.01); *A61M 2016/0039* (2013.01); *A61M 2202/02* (2013.01); *A61M 2202/04* (2013.01); *A61M 2202/064* (2013.01); *A61M 2205/8206* (2013.01); *A61M 2205/8218* (2013.01); *A61M 2205/8287* (2013.01)

(56) References Cited

U.S. PATENT DOCUMENTS

| | | | |
|---|---|---|---|
| 3,926,343 A | 12/1975 | Kleiner | |
| 4,949,715 A | 8/1990 | Brugger | |
| 6,143,277 A * | 11/2000 | Ashurst | A61M 15/009 424/45 |
| 2005/0247305 A1 | 11/2005 | Zierenberg et al. | |
| 2006/0201499 A1 | 9/2006 | Muellinger et al. | |
| 2007/0074722 A1* | 4/2007 | Giroux | A61M 11/06 128/203.15 |
| 2007/0282276 A1 | 12/2007 | Boeck et al. | |
| 2009/0064997 A1 | 3/2009 | Li | |
| 2009/0145432 A1 | 6/2009 | Braithwaite | |
| 2011/0041844 A1* | 2/2011 | Dunne | A61M 11/007 128/203.12 |

FOREIGN PATENT DOCUMENTS

| | | |
|---|---|---|
| WO | WO03045483 | 6/2003 |
| WO | WO 09038703 A1 | 3/2009 |
| WO | WO2011153261 | 12/2011 |
| WO | WO2013/065503 A | 5/2013 |
| WO | WO 2013/098334 | 7/2013 |
| WO | WO2013128447 | 9/2013 |

OTHER PUBLICATIONS

International Search Report dated Dec. 10, 2014.
European Office Action dated Jan. 4, 2019.
Indian Office Action dated Dec. 22, 2020.

* cited by examiner

OPERATED NEBULIZER AND MEANS THEREOF

FIELD OF THE INVENTION

The present invention is related to a novel operated nebulizer, more particularly to a novel operated nebulizer, comprising an air actuator adapted for releasing a flow of compressed air at such time as a predetermined pressure has been reached and further a nozzles system for medication distribution having a predetermined droplets size.

BACKGROUND OF THE INVENTION

Inhaled medication is the first-line treatment of diseases such as asthma or chronic obstructive pulmonary disease. Its effectiveness is related to the amount of drug deposited beyond the oropharyngeal region, the place where the deposit occurs and its distribution.

It is further important to consider the size of the inhaled particles, the breathing conditions, the geometry of the airways, and the mucociliary clearance mechanisms.

Nebulizers allow high doses administration of medication in patients who are not able to coordinate or cooperate and they are further able to administer several substances mixed together in one same solution. It is known that the minimal inspiratory flow needed for the aerosol produced by a nebulizer to reach the lungs is about 6-8 l/min. However, there are high amounts of drug lost as much of the medication is retained in the nebulizer dead-space, or it is lost in the room air during expiration. It has further been estimated that only 10% of the dose that is initially placed in the nebulizer will be effectively deposited in the lungs. The large droplets are deposited in the oropharynx, while the droplets are too small to penetrate in the lungs and are once again expelled during expiration.

U.S. patent app. No 2005247305 discloses a nebulizer having an insertable container and a monitoring device for counting actuations of the nebulizer is proposed. The monitoring device is mounted in a detachable housing part and directly detects movements of container during a nebulizing process, an air supply current in the region of a mouthpiece, and/or the production of aerosol, in order to detect this as the actual dispensing of fluid and actuation of the nebulizer, while preferably the time of actuation of the nebulizer is additionally detected and stored. This allows better monitoring and guidance for the user.

U.S. patent application No. 2007282276 presents a process and a device for dosing a pharmaceutical agent in particular as an aerosol, with enhanced dosing accuracy. To achieve an enhanced dosing accuracy, a first component is produced in batches and combined with a second component, such as a guide pipe selected from a suitable group guide pipes. The suitable group of second components is selected based on at least one decisively significant value of the respective batch first components and is distinguished by an essential value of the second component which will optimize the sealing between the first and second components.

WO2013098334 discloses a device for enabling a user to inhale at a desired inspiratory flow rate and/or pressure, comprising a feedback system configured to indicate to a user by means of a signal during an inhalation manoeuvre whether an inhalation parameter, such as the inspiratory flow rate, is within a predefined target range. The signal may be an optical or a non-optical signal, such as a light signal, an acoustic signal, or a tactile signal.

U.S. patent application No. 2006201499 discloses a device for the application of a pharmaceutical via the lung comprising a control and an air pump connected to the control, the air pump being controlled by the control such that it supplies an inhalation flow, or inhalation volume or both according to a predetermined time course to a nebulizer connected to the air pump.

The above-described devices do not provide a drug deposition having a defined particle size thus, provide a long treatment time.

It therefore remains a long felt and unmet need to provide novel means and methods for a nebulizer device which allows the deposition of inhaled drugs in more effective and short term manner based on the size of the drug particles.

SUMMARY OF THE INVENTION

It is an object of the present invention to disclose a nebulizer for dispensing a consecutively dose of a medicament in the form of a mist, comprising:

a. an energy source (ES) selected from the group consisting of: LG source, electric motor, electric linear actuator, electromagnetic solenoid based actuator, spring operated mechanism, hydraulic pump, compressed gas (CG), flywheel, steam engine, carnot machine, stirling cycle and a combination thereof;
b. an air-containing volume;
c. an air outlet fluidly connected to said air-containing volume;
d. an air actuator adapted to release a flow of compressed air through said air outlet at such time as a predetermined ES pressure has been reached in said volume; and
e. at least two valve means in communication with said air actuator;

wherein said compressed air is released at a predetermined pressure of about 20 to about 100 psig; further wherein said valve means controls the actuation of said air actuator such that when a medication is nebulized, a mist distribution of a medication is formed having droplets size in the range of approximately 1 μm to approximately 7 μm which inhaled by a user at a set of predetermined intervals.

It is another object of the present invention to provide the nebulizer as defined in any of the above, wherein additionally comprising a volume adapted to contain LG, said volume fluidly connected to a LG source.

It is another object of the present invention to provide the nebulizer as defined in any of the above, wherein said air is released at a predetermined pressure of about 20 to about 100 psig whilst said LG-expending volume contains a first compressed LG compressed between about 20 and about 4000 psig.

It is another object of the present invention to provide the nebulizer as defined in any of the above, wherein said droplets are released in a quick succession form at a periodically rate of about 2.5 ml droplets of said medication per 2 minutes.

It is another object of the present invention to provide the nebulizer as defined in any of the above, wherein said valve means comprises at least one control valve having an idle state and an automatic state and at least two directing valves configured to identify and control said actuator movement, position and direction.

It is another object of the present invention to provide the nebulizer as defined in any of the above, wherein said at least two directing valves are based on ferromagnetic mechanism.

It is another object of the present invention to provide the nebulizer as defined in any of the above, wherein said actuator is partially composed of ferromagnetic material.

It is another object of the present invention to provide the nebulizer as defined in any of the above, wherein said air actuator is separating LG-containing volume from air-containing volume; the air actuator is further facilitating said dose airflow by allowing the expansion of said LG in said at least one LG-expending volume from its condensed liquid phase to its expanded gas phase.

It is another object of the present invention to provide the nebulizer as defined in any of the above, wherein said air actuator is selected from a group consisting of a piston pump, a turbine, a rotor, an inflatable membrane spring and a combination thereof.

It is another object of the present invention to provide the nebulizer as defined in any of the above, wherein said valve means additionally comprising an ES valve in a fluid connection with said ES; said ES valve configured to control the movement of said actuator.

It is another object of the present invention to provide the nebulizer as defined in any of the above, wherein additionally comprising an energy source selected from the group consisting of: electric motor, electric linear actuator, electromagnetic solenoid based actuator, spring operated mechanism, hydraulic pump, compressed gas (CG), flywheel, steam engine, carnot machine, stirling cycle and a combination thereof.

It is another object of the present invention to provide the nebulizer as defined in any of the above, wherein said air actuator is configured to control the flow of the compressed air after buildup of a predetermined pressure.

It is another object of the present invention to provide the nebulizer as defined in any of the above, wherein said nebulizer additionally comprising an air inlet.

It is another object of the present invention to provide the nebulizer as defined in any of the above, wherein said nebulizer additionally comprising an LG outlet.

It is another object of the present invention to provide the nebulizer as defined in any of the above, wherein said membrane, when inflated by said LG source, compresses air flow via said air outlet.

It is another object of the present invention to provide the nebulizer as defined in any of the above, wherein said membrane is configured as a diaphragm-like shape or a condom-like shape.

It is another object of the present invention to provide the nebulizer as defined in any of the above, wherein said nebulizer additionally comprising at least two nozzles in a fluid connection with said air outlet.

It is another object of the present invention to provide the nebulizer as defined in any of the above, wherein said nozzle type is selected from the group consisting of venturi nozzle, laskin nozzle, annular flow high velocity, colliding streams nozzle, additive energy nozzles, swirl nozzle and a combination thereof.

It is another object of the present invention to provide the nebulizer as defined in any of the above, wherein said at least two nozzles are interconnected in an angle $\alpha,\beta<90°$.

It is another object of the present invention to provide the nebulizer as defined in any of the above, wherein the LG source is selected from the group consisting of liquefied petroleum gas (LPG), propane, butane and a combination thereof.

It is another object of the present invention to provide the nebulizer as defined in any of the above, wherein said nebulizer additionally comprising a medicament metering mechanism comprising a medicament chamber and metering valve; the metering valve is in a fluid connection with the medicament chamber.

It is another object of the present invention to provide the nebulizer as defined in any of the above, wherein the medicament is in a form selected from the group consisting of solid form, gas form, liquid form and a combination thereof.

It is another object of the present invention to provide the nebulizer as defined in any of the above, wherein the nebulizer is administrated in a manner selected from the group consisting of: systemic administration via patient's lungs, topical administration, and a combination thereof.

It is another object of the present invention to provide the nebulizer as defined in any of the above, wherein the nebulizer is configured for spraying one or more members of a group consisting of gas materials, liquid materials, fine particles, powder materials and a mixture thereof.

It is another object of the present invention to provide the nebulizer as defined in any of the above, wherein the nebulizer is a portable and handheld device.

It is another object of the present invention to provide the nebulizer as defined in any of the above, wherein the nebulizer is used for treating asthma, chronic obstructive pulmonary disease (COPD) and other respiratory diseases and conditions.

It is another object of the present invention to provide the nebulizer as defined in any of the above, wherein the nebulizer is activated manually, semi manually or electrically.

It is another object of the present invention to provide the nebulizer as defined in any of the above, wherein the nebulizer further comprising a power source selected from the group consisting of a battery, an electric source, a rechargeable battery, an electric motor and a combination thereof.

It is another object of the present invention to provide the nebulizer as defined in any of the above, wherein the actuator is configured to control a steady mist distribution of a medication having droplets size less than about 5 μm.

It is another object of the present invention to provide the nebulizer as defined in any of the above, wherein the nebulized additionally comprising a breath actuation means which responds to inhalation by the subject when sense subject's breath.

It is another object of the present invention to provide the nebulizer as defined in any of the above, wherein the breath actuation means is configured to sense negative pressure of patient inhalation and using that sensing to trigger or initiate high pressure gas flow, the breath actuation means is selected from the group consisting of pressure sensor, Intake Air Temperature (IAT) sensor and a combination thereof.

It is another object of the present invention to provide the nebulizer as defined in any of the above, wherein additionally comprising spring means in communication with the actuator, the spring means is selected from a group consisting of mechanical spring, gas loaded spring, gas pressure and a combination thereof.

It is another object of the present invention to provide the nebulizer as defined in any of the above, wherein the spring means is in communication with the air actuator such that (i) as a container is filled with the LPG, the spring is loaded; and, (ii) the dispensing of the medication from the container is provided by the application of a force upon the actuator, by means of the spring with the LPG.

It is another object of the present invention to provide the nebulizer as defined in any of the above, wherein the spring means functions according to a push and pull mechanism such that the spring means is configured to return the actuator to its forward position and further restart the cycle and move it rearward.

It is another object of the present invention to disclose a nozzles system for dispensing a consecutively dose of a medicament in the form of a mist, comprising:
a. a nebulizer comprising:
   i. an energy source (ES) selected from the group consisting of: LG source, electric motor, electric linear actuator, electromagnetic solenoid based actuator, spring operated mechanism, hydraulic pump, compressed gas (CG), flywheel, steam engine, carnot machine, stirling cycle and a combination thereof;
   ii. an air-containing volume;
   iii. an air outlet fluidly connected to the air-containing volume;
   iv. an air actuator adapted to release a flow of compressed air through the air outlet at such time as a predetermined ES pressure has been reached in the volume; and
   v. at least two valve means in communication with the air actuator;
b. at least two nozzles in fluid communication with the air outlet;
wherein the nozzles are venturi nozzles arrange in a predetermined angle such that the droplet size of a medication dispersed from the nebulizer is in a range of about 1 μm to about 7 μm.

It is another object of the present invention to provide the nozzles system as defined in any of the above, wherein nozzles are configured to disperse at least 2.5 ml of the medication in approximately 2 minutes.

It is another object of the present invention to provide the nozzles system as defined in any of the above, wherein the at least two nozzles are interconnected in a vertically or horizontally manner to each other.

It is another object of the present invention to provide the nozzles system as defined in any of the above, wherein the nozzle type is selected from the group consisting of laskin nozzle, annular flow high velocity, colliding streams nozzle, additive energy nozzles, swirl nozzle and a combination thereof.

It is another object of the present invention to provide the nozzles system as defined in any of the above, wherein the nozzles are with a diameter of about 0.2 mm to about 0.8 mm configured to disperse a droplets size less than 5 μm vs the released dose or medication.

It is another object of the present invention to provide the nozzles system as defined in any of the above, wherein at least one nozzle is configured with a diameter of about 0.5 mm to provide a droplets distribution of more than 70% of the medication.

It is another object of the present invention to provide the nozzles system as defined in any of the above, wherein at least one nozzle is with a diameter of about 0.5 mm to disperse a droplets size is in a range of about 2 μm to about 3 μm.

It is another object of the present invention to provide the nozzles system as defined in any of the above, wherein the at least two nozzles interconnected in a vertical angle generate a mist of about 80% droplets smaller than 3 μm.

It is another object of the present invention to provide the nozzles system as defined in any of the above, wherein the at least two nozzles interconnected in a vertical angle generate a mist of about 90% droplets smaller than 5 μm.

It is another object of the present invention to disclose a nebulizer for improving medicament's alveolar deposition, comprising:
at least one inlet of liquefied gas (LG) communicating with at least one first volume for LG-expansion;
at least one second volume for containing a medicament, the second volume is in fluid connection with at least one medicament outlet;
an air actuator configured for moving air and the medicament towards patient's respiratory tract;
a valve means in communication with the air actuator;
a container with a liquefied LG source, the container is in fluid connection with the first volume, where the LG is allowed to gasify, via the at least one LG inlet;
wherein the air actuator comprises an LG-blocking member separating the first volume where LG is in liquid phase and the second volume where the LG is in its gas phase; further wherein the LG-blocking member moveable towards the medicament outlet by the valve means and a pressure exerted by the LG-phase transition, thereby emitting effective measure of about 0.1 ml to about 3 ml of the medicament in less than about 6 minutes.

It is another object of the present invention to provide the nebulizer as defined in any of the above, wherein nozzles are configured to disperse at least 2.5 ml of the medication per 2 minutes.

It is another object of the present invention to provide the nebulizer as defined in any of the above, wherein the air actuator is selected from a group consisting of a piston pump, a turbine, a rotor, an inflatable membrane and a combination thereof.

It is another object of the present invention to provide the nebulizer as defined in any of the above, wherein the air outlet is provided with an orifice having a diameter of about 0.5 mm to about 1.5 mm, operably configured to emit effective measure of the medicament having average particles size equal to or less than 5 μm.

It is another object of the present invention to provide the nebulizer as defined in any of the above, wherein the LG is with a pressure operably configured to emit effective measure of the medicament having average particles size equal to or less than 5 μm.

It is another object of the present invention to provide the nebulizer as defined in any of the above, wherein the second volume is with a volume operably configured to emit effective measure of the medicament having average particles size equal to or less than 5 μm.

It is another object of the present invention to provide the nebulizer as defined in any of the above, wherein the LG blocking member is with a speed of movement operably configured to emit high medicament quantity having average particles size equal to or less than 5 μm.

It is another object of the present invention to disclose a method of improving medicament's alveolar deposition characterized by the following steps:
a. providing a nozzles system for dispensing a consecutively dose of a medicament in the form of a mist, comprising: a nebulizer an energy source (ES) selected from the group consisting of: LG source, electric motor, electric linear actuator, electromagnetic solenoid based actuator, spring operated mechanism, hydraulic pump, compressed gas (CG), flywheel, steam engine, carnot machine, stirling cycle and a combination thereof; an air-containing volume; an air outlet fluidly connected to the air-containing volume; an air actuator adapted to release a flow of compressed air through the air outlet at such time as a predetermined ES pressure has been reached in the volume; at least two valve means in communication with the air actuator; and at least two nozzles in fluid communication with the air outlet; releasing the liquefied ES directly to the actuator, thereby actuating the actuator; and b. facilitating the flow of an effective measure of the medicament towards the alveoli via patient's respiratory tract.

It is another object of the present invention to provide the method as defined in any of the above, wherein the method additional comprising step of providing at least two nozzles interconnected in a predetermined angle such that the droplet size of a medication dispersed from the nebulizer is in a range of about 1 µm to about 7 µm; further wherein nozzles are configured to disperse at least 2.5 ml of the medication in approximately 2 minutes.

It is another object of the present invention to provide the method as defined in any of the above, wherein the method additionally comprising step of reducing, by means of the medicament dispensing nozzle, the average particle size of the medicament outflow to value being equal to or less than 5 mm, followed by a step of facilitating the flow of the medicament.

It is another object of the present invention to provide the method as defined in any of the above, wherein the method additionally comprising step of selecting the air actuator from a group consisting of a piston pump, a rotor, a turbine, an inflatable membrane and a combination thereof.

It is another object of the present invention to provide the method as defined in any of the above, wherein the method additionally comprising step of selecting the LG from a group consisting of liquefied petroleum gas (LPG), propane, butane and a mixture thereof.

It is another object of the present invention to provide the method as defined in any of the above, wherein the method additionally comprising step of providing at least one control valve having an idle state and an automatic state and at least two directing valves configured to identify and control the actuator movement, position and direction.

It is another object of the present invention to provide the method as defined in any of the above, wherein the method additionally comprising step of providing a medicament selected from a group consisting of solid form, gas form, liquid form and a mixture thereof.

It is another object of the present invention to provide the method as defined in any of the above, wherein the method additionally comprising step of configuring the nebulizer for spraying at least one dose form selected from the group consisting of a gas material, a flow material, fine particles, a liquid material, a powder material and a mixture thereof.

It is another object of the present invention to provide the method as defined in any of the above, wherein the method additionally comprising step of introducing the nebulizer to the topical system or the systemic system via patient's lungs.

It is another object of the present invention to provide the method as defined in any of the above, wherein the method additionally comprising step of providing the at least two nozzles interconnected in an angle $\alpha, \beta < 90°$.

BRIEF DESCRIPTION OF THE DRAWINGS

In the following description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

In the accompanying drawing.

DETAILED DESCRIPTION OF THE PREFERRED EMBODIMENTS

The present invention have been defined specifically to provide device, means and method for a nebulizer device and system for spraying a dose form, comprising: a gaseous propellant, actuator means configured to release a flow of compressed air after a predetermined liquefied gas (LG) pressure has been reached and, an air outlet. The actuator means operated by the activated liquefied gas (LG) pressure in order to compress air via the air outlet. The actuator means builds up a pressure on the air delivery side for causing a dose of airflow.

The present invention provides a nebulizer drug delivery system which improves lung deposition whilst at same time, increase lung bioavailability hence, overall systemic absorption. The nebulizer of the present invention further solves the problem of nebulizers which deliver medication continuously by using the patient's breathing cycle to automatically control the delivery of medication to patient's lungs.

Figure 1A:
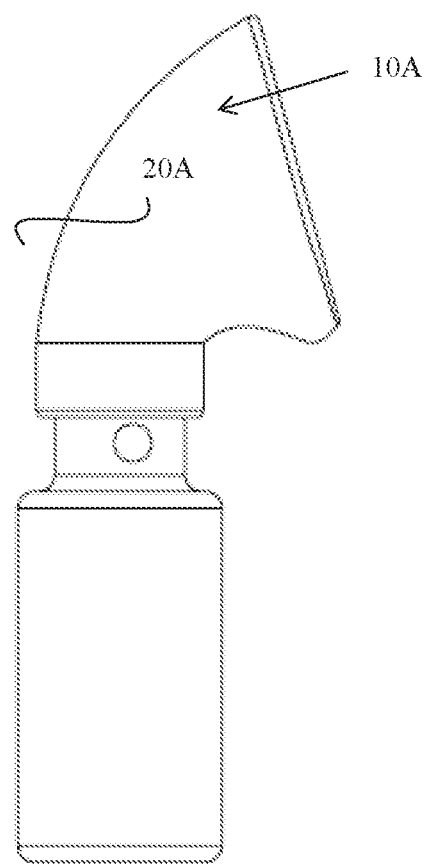
FIGS. 1A-B present a schematic view of a nebulizer system of the present invention.
Figure 1B:
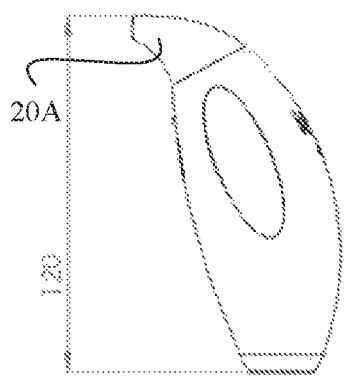

Reference is now made to FIGS. 1A-B which illustrate a schematic view of a nebulizer housing device 10A comprising a breath actuated mode via mouthpiece or mask interface 20A for covering subject's breathing system. The nebulizer of the present invention may be an electric- or battery-powered device that turn liquid medicine into a fine mist that's inhaled into the lungs.

The present invention provides a nebulizer for dispensing a consecutively dose of a medicament in the form of a mist, comprising: an energy source (ES) selected from the group consisting of: LG source, electric motor, electric linear actuator, electromagnetic solenoid based actuator, spring operated mechanism, hydraulic pump, compressed gas (CG), flywheel, steam engine, carnot machine, stirling cycle and a combination thereof, an air-containing volume; an air outlet fluidly connected to the air-containing volume; an air actuator adapted to release a flow of compressed air through the air outlet at such time as a predetermined ES pressure has been reached in the volume and at least two valve means in communication with the air actuator.

The compressed air is released at a predetermined pressure of about 20 to about 100 psig. Furthermore, the valve means controls the actuation of the air actuator such that when a medication is nebulized, a mist distribution of a medication is formed having droplets size in the range of approximately 1 µm to approximately 7 µm which inhaled by a user at a set of predetermined intervals.

In another embodiment of the present invention, the nebulizer further comprising: an air actuator comprising at least one inlet of liquefied gas (LG), at least one air outlet, at least one first LG-expanding volume and at least one second air-containing volume. The first and second volumes are effectively separated by means of an LG-blocking member.

The nebulizer may further comprise a container with LG source. The container is in a fluid connection with LG-expanding volume via at least one LG inlet. The air actuator is facilitating the dose of airflow by allowing the expansion of the LG in at least one LG-expanding volume from its condensed liquid phase to its expanded gas phase.

Furthermore, the expansion of the LG facilitates the compression of the air within the at least one air-containing volume, such that a dose of LG-free air flow is inhalable via the at least one air outlet. The nebulizer is configured such that when the nebulizer in use it is positioned at a location to be placed within a patient's oral cavity and further received in the mouth of a subject.

The Nebulizer of the present invention may further use LG to break up medical solutions and suspensions into small aerosol droplets that can be directly inhaled from the mouthpiece of the device.

In another embodiment of the present invention, the nebulizer is a portable and handle hand device and is effective for short and long treatment. Furthermore, the nebulizer provides an improved lung deposition. The nebulizer is constructed such that the actuator allows the delivery of a sufficient amount of a compressed air and directs the compressed air flow in such manner toward the air outlet such that an entire mass of a latter is released from the nebulizer.

In another embodiment of the present invention, the LG is preferably Liquefied petroleum gas, also known as LPG, GPL, LP Gas, liquid petroleum gas or simply propane or butane. The LPG is a flammable mixture of hydrocarbon gases used as an aerosol propellant. The LG may be further activated using a valve 12.

In another embodiment of the present invention, the nebulizer the present invention may comprise a compressed or pressurized gas.

The LG is further selected from the group consisting of: 1,1,1,2-tetrafluoroethane (HFA 134a) or 1,1,1,2,3,3,3-heptafluoropropane (HFA 227) or a mixture thereof. In alternative propellants such as carbon dioxide or other which are gaseous at room temperature and standard atmospheric pressure may be used.

The nebulizer may further comprise a system for delivering a medicament, the system may comprise an additionally medicament chamber for loading a medicament and a medication metering valve for releasing the medicament from the chamber. The medication metering valve is in fluid connection with the medicament chamber. The breath actuated valve is configured to deliver a specific amount of medicament to the patient's lungs. The medicament may be delivered in a form of a short burst of aerosolized medication which is inhaled by the patient.

Figure 2A:
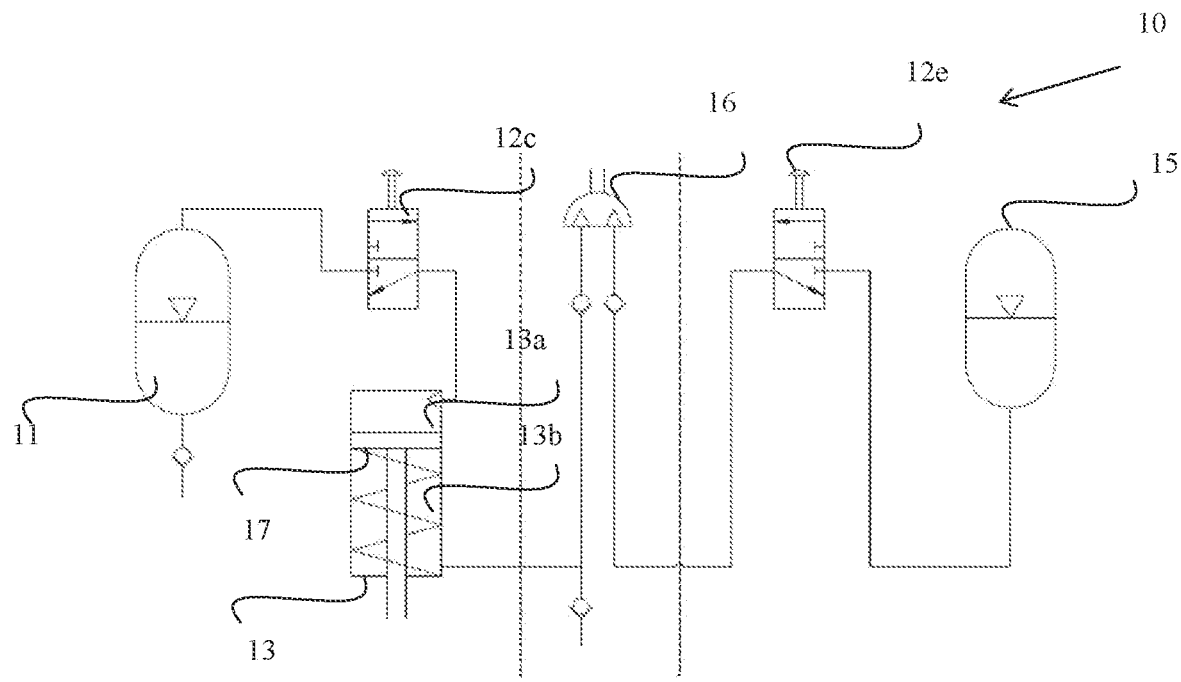
FIGS. 2A-C present a schematic view of an air pressure-operated nebulizer for spraying a burst of dose forms, of the present invention.
Figure 2B:
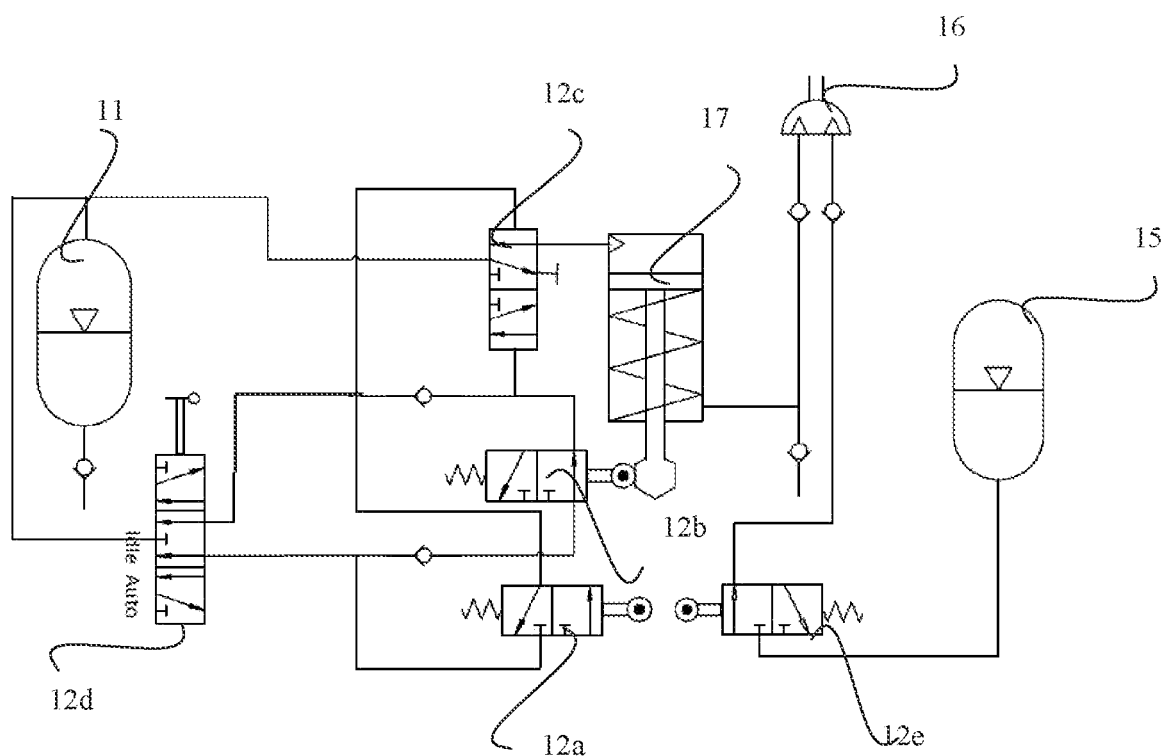
Figure 2C:
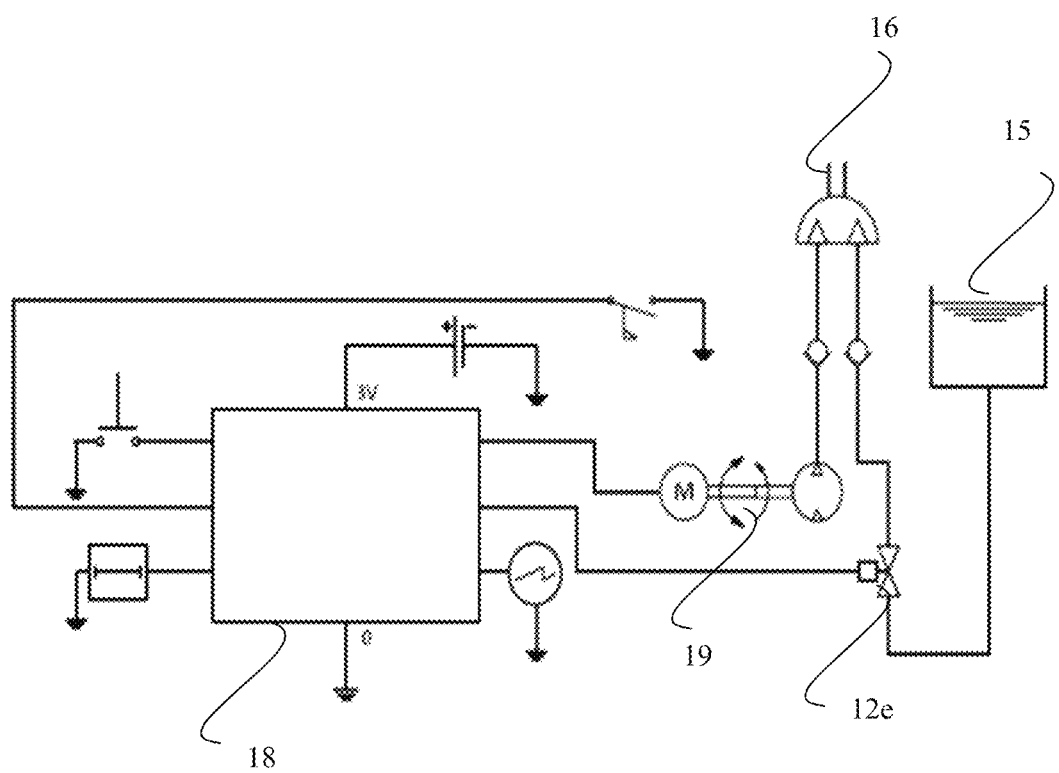

Reference are now made to FIGS. 2A-C which illustrate an air pressure-operated nebulizer system for spraying a predefined dose form, comprising: (a) an energy source (ES) such as a liquefied gas (LG) source 11, (b) a volume adapted to contain LG 13a, the volume is fluidly connected to the LG source 11, (c) an air-containing volume 13b (d) at least one air outlet fluidly connected to air-containing volume, (e) actuator means 17 separating the LG-containing volume from the air-containing volume and, valve means 12 in communication with the air actuator.

In another embodiment of the present invention, the air actuator is selected from a group consisting of a piston pump, a rotor, a turbine, an inflatable membrane, a spring, and a combination thereof. The actuator may be further integrated with spring means. The spring means is in communication with the air actuator such that (i) as a container is filled with LG, the spring is loaded and, (ii) the dispensing of the air from the container is provided by the application of a force upon the actuator, by the compressed LG and further by the spring means.

The spring means may further control the rotation of the actuator. The spring means is selected from a group consisting of: mechanical spring, gas loaded spring, gas pressure, or any other method known to one skilled in the art. The spring means may be configured as a pressurizing recoil which is dependent upon the pressure provided by the actuator. Once a container is filled with a medication, the spring is loaded, such that the same is activated, the spring applies pressure upon the actuator so as to release predetermined amount of the medication in continuously.

In another embodiment of the present invention, the valve means is synchronized with subject's breath such that when a medication is nebulized, a mist distribution of a effective measure of medication is formed having droplets size in the range of approximately 1 µm to approximately 7 µm which inhaled by a user at a set of predetermined intervals (e.g, at least one interval may be of at least 1 to 3 minutes). The droplets are released in a quick succession form at a periodically rate of about 0.1 ml to about 3 ml droplets of the medication in less than about 6 minutes. The droplets are preferably released in a quick succession form at a periodically rate of about 2.5 ml droplets of the medication per approximately 2 minutes.

FIG. 2B further illustrates the nebulizer system comprising valve means designated herein in a predefined arrangement adjacent to the nebulizer LG inlet having high pressure LG supplied directly to the valve so that when at least one of valve is opened in response to system determinations, the gas at high pressure can be substantially immediately delivered at a steady state of flow and pressure to the nebulizer unit to nearly or substantially instantaneously begin nebulization producing the proper distribution range and of particle sizes at a desired density. The valve means further comprising at least one control valve 12d and at least three directing valves 12a,12b,12c. The control valve 12d comprises an idle state and an automatic (auto) state for activating the nebulizer. The directing valves 12a,12b,12c control and further monitor the actuator movement in the axial direction whilst LG is released by the LG-directing valve 12c to the LG-expanding volume and further forcing the actuator to downward position. The directing valves 12b,12a are based upon ferromagnetic mechanism such that when the actuator is forced to a downward position valve 12b pulls down the actuator and when the actuator reaches to valve 12a the actuator is released back to its rest position. The valve means further comprising a medication metering valve 12e which controls the medication release from the medication container 15 to a nozzles system 16.

FIG. 2C further demonstrates a schematic view of the electric system of the nebulizer further comprising an energy/propellant source 19, and a controller 18 for controlling and activating the breath actuating system, the motor, the medication metering, the counter/timer, and the valve means in the nebulizer system.

In another embodiment of the present invention, the actuator means is adapted to release a flow of compressed air through the air outlet at such time as a predetermined LG pressure has been reached in the volume adapted to contain LG. The LG and the air remain separate at all times. Furthermore, the compressed air is released at a predetermined pressure of about 20 and about 100 psig whilst the LG-expending volume contains a first compressed LG compressed between about 20 and about 4000 psig. The LG may further be compressed in a pressure of about 50 to 4000 psig. The airflow released from the nebulizer outlet depended upon differential pressure gauges between the one LG-expanding volume and the air-containing volume separated by means of an LG-blocking member.

The LG-expanding volume is adapted for containing a compressed LG at a first pressure.

The air containing volume may be in a selective communication with LG-expanding volume. The air containing volume is adapted for containing a compressed air at a second pressure less than the first pressure. Both of the volumes are cooperating so as to yield a second pressure of the compressed air within the air containing volume. The LG-expanding volume contains a compressed LG compressed in the range of about 20 to about 200 psig, and the air containing volume contains compressed air compressed in the range of about 3 to about 10 psig.

As used herein the term "about" or "approximately" denotes ±25% of the defined amount or measure or value.

The term "effective measure" of a medicament refers hereinafter to a medicament dose to be delivered towards patient's respirator tracks, wherein the dose is sufficient for curing the patient according to a predefined treatment protocol. It is well within the scope of the invention, where effective measure ranges from 1 microgram to 1 gram. It is further in the scope of the invention, where effective measure of the medicaments is provided when characterized by an average particles size of less than about 5 μm. Additional or alternatively, it is in the scope of the invention, where effective measure of the medicaments is characterized by a homogeneous medicament, i.e., one or more medicaments introduced to patient's respiratory tract by air carrier, and not another carrier, such as a carbon-containing liquefied gas (carbon dioxide, butane, propane etc.).

Additional or alternatively, it is in the scope of the invention, where effective measure of the medicaments is a minimal dose useful for providing enhanced medicament absorption and kinetics per internal surface area of patient's alveoli. Additional or alternatively, it is in the scope of the invention, where effective measure of the medicaments is characterized by an average particles size (APS) μm, wherein the inhaled medicament is sized equal or less the APS to absorbed more than 50% per internal surface area in the alveoli. According to an embodiment of the invention the average particles size is in a range 0.75 μm≤APS≤7.0 μm. Furthermore, a differential pressure gauge is further created between the outlet and inlet ports, each connected to one of the volume portions whose pressure is to be monitored.

The term 'medication', 'medicament', 'medicine', 'drug', as used herein, refers to any chemical or natural substance formulated or compounded as single active ingredient or in combination of other pharmacologically active substance, it may be in a separate but packed in a single unit pack as combination product intended for internal, or external or for use in medical diagnosis, cure, treatment, prevention of disease, disorder or to enhance physical or mental well-being. The chemical or natural substance may be in a form selected from the group consisting of solid form, gas form, liquid form and any combination thereof.

Without wishing to be bound by theory, the size and shape of particles are primordial factors that condition their deposition in the lungs. The size is defined by the mass median aerodynamic diameter (MMAD) or diameter of a particle of mass equal to the average particle diameter of a population, meaning the diameter of a particle in which 50% of the aerosol mass is greater and the other 50% is smaller. Depending on their size and shape, the particles can be deposited by means of four mechanisms: Impaction which is a physical phenomenon by which the particles of an aerosol tend to continue on a trajectory when they travel through the airway, instead of conforming to the curves of the respiratory tract. Particles with enough momentum (product of the mass and velocity) are affected by centrifugal force at the points where the airflow suddenly changes direction, colliding with the airway wall. This mainly happens in the first 10 bronchial generations, where the air speed is high and the flow is turbulent This phenomenon mainly affects particles larger than 10 μm, which are mostly retained in the oropharyngeal region, especially if the drug is administered by dry powder nebulizers (DPI). Interception which is mainly related to fibers, which, due to their elongated shape, are deposited as soon as they contact the airway wall. Sedimentation which is a physical phenomenon by which particles with sufficient mass are deposited due to the force of gravity when they remain in the airway for a sufficient length of time. This predominates in the last 5 bronchial generations, where the air speed is slow and the residence time is therefore longer.

Suspension which is a phenomenon by which the particles of an aerosol move erratically from one place to another in the airways. This happens as a consequence of the Brownian diffusion of particles with an MMAD smaller than 0.5 μm when they reach the alveolar spaces, where the air speed is practically zero. These particles are generally not deposited and they are expelled once again upon exhalation. It can generally be considered that particles with an MMAD higher than 10 μm are deposited in the oropharynx, those measuring between 5 and 10 μm in the central airways and those from 0.5 to 5 μm in the small airways and alveoli. Therefore, for topical respiratory treatment it is best to use particles with an MMAD between 0.5 and 5 μm. The nebulizer of the present invention enables a breathable fraction of a medication mist having a droplets distribution adjustable between one or more of the following rangers: 0.5-7.5 μm, 0.5-2.5 μm, 2.5-5.0 μm or 5.0-7.5 μm.

In another embodiment of the present invention, the deposition of fluid particles of the nebulizer of the present invention is proportional to the inspiratory flow. This is due to the fact that the increased inspiratory flow reduces the residence time of the particles in the airway, therefore the effects of the severity and of the Brownian movement will be quite lower. A minimal inspiratory flow is necessary to drag the particles toward the interior of the bronchial tree.

In another embodiment of the present invention, the nebulizer of the present invention further comprises inlets and outlets having an optimize diameter which allow correlation between droplets size medication dose and further droplets distribution in a predefined velocity and time.

According to one embodiment of the present invention, the nebulizer system comprises a medication container. The medication is selected from the group consisting of granular matter, a drug sized to form fine particles, powder, sol, gel, sol-gel, glass, encapsulated matter, milled composition or any combination thereof. Alternatively or additionally, the medicament may be utilized in a liquid phase. In such a case, the fluid is selected in a non-limiting manner from water miscible compositions, water immiscible compositions, emulsions, extracts, dispersions, suspensions, vasiculated solutions, aggregated phases or any combination thereof. It is according to another embodiment of the present invention wherein the fluid or medicament is selected in a non-limiting manner from at least one of the group of Braochodilators, especially sympatic mimetics, alfa antagonists, anti cholinergics; nasal decongestants, such as pseudoehedrines, ephedrines; steroids; anti histamines; anti prostaglandins, alternative or homeopathic medicaments; vaso constrictors; local anesthetics; mast cell stabilizers; antibiotics, such as biocides, fungicides etc; pleasant odor; pheromones; hormone treatments, such as ADH, insulin, growth hormones; vapors, humidifiers; drying compositions; hot or cold vapors; hyper-, iso- or hypotonic vapors or any combination thereof, or decongestants, essential oils, volatile compounds, etheric oils, terepenes, terpanols and either water miscible or water-immiscible extracts, especially oils or extracts.

In another embodiment the nebulizer may further be adapted for treating asthma, chronic obstructive pulmonary disease (COPD) and other respiratory diseases and conditions. The medicament may be in a form selected from the group consisting of solid form, gas form, liquid form and any combination thereof.

According to one embodiment of the present invention, the nebulizer is further configured to deliver a medicament for treating chronic inflammatory diseases such as asthma, as presented in Table 1 below:

TABLE 1

| Category | Purpose | Medicament types |
|---|---|---|
| Long-term asthma control medicaments | Taken regularly to control chronic symptoms and prevent asthma attacks - the most important type of treatment for most people with asthma | Inhaled corticosteroids Leukotriene modifiers Long-acting beta agonists (LABAs) Theophylline Combination nebulizers that contain both a corticosteroid and a LABA |
| Quick-relief medicaments (rescue medicaments) | Taken as needed for rapid, short-term relief of symptoms - used to prevent or treat an asthma attack | Short-acting beta agonists such as albuterol Ipratropium (Atrovent) Oral and intravenous corticosteroids (for serious asthma attacks) |
| Medicaments for allergy-induced asthma | Taken regularly or as needed to reduce your body's sensitivity to a particular allergy-causing substance (allergen) | Allergy shots (immunotherapy) Omalizumab (Xolair) |

Other medicaments may further be adapted, selected from the group consisting of: Bronchodilators Short-acting bronchodilators (including: Anticholinergics (such as ipratropium), Beta2-agonists (such as albuterol and levalbuterol)), a combination of the two Long-acting bronchodilators, (including: Anticholinergics (such as tiotropium), Beta2-agonists (such as salmeterol, formoterol, and arformoterol)), Phosphodiesterase-4 (PDE4) inhibitors, Corticosteroids (such as prednisone), Expectorants, (such as guaifenesin (Mucinex)), Methylxanthines.

Other medicaments may further be adapted for treating Chronic obstructive pulmonary disease (COPD), selected from the group consisting of: Aclidinium inhalation, aclidinium/formoterol inhalation, AM211, AZD1981 (CRTh2 receptor antagonist), AZD 2115 (MABA), AZD2423 (CCR2b antagonist), AZD3199(iLABA), AZD5069 (CXCR2), AZD5423, AZD3199, AZD5069(CXCR2), AZD5423 (inhaled SEGRA), AZD8683(muscarinic antagonist), BCT197, B1-137882, B10-11006, Dulera mometasone/formoterol, EP-101(LAMA), EP-102(LAMA/LABA), EPI-12323, formoterol/fluticasone fixed-dose combination (inhalation), GSK256066 (inhaled PDE4 inhibitor), GSK573719 (muscarinic acetylcholine antagonist), GSK573719/vilanterol (muscarinic acetylcholine antagonist/long-acting beta2 agonist), GSK610677 (inhaled p38 kinase inhibitor), GSK961081 (muscarinic antagonist/beta2 agonist), GSK1325756 (chemokine receptor antagonist-2), GSK2245840 (SIRT1 activator), Ilaris canakinumab, LAS 100977(LABA), levosalbutamol/ipratropiuminhalation solution, losmapimod (oral p38 kinase inhibitor), MEDI-2338 (anti-IL-18 mAb), MEDI-8968 (anti-IL-1R), MK-7123 (navarixin), MN-166(ibudilast), MN-221(bedoradrine), NVA237 (glycopyrrolate inhalation), O-desulfated heparin intravenous, olodaterol, olodaterol/tiotropium bromide, paclitaxel-loaded stent, PF-03715455, PH-797804, Prochymal remestemcel-L, PT001 (glycopyrrolate inhalationaerosol), PT003 (glycopyrrolate/formoterol inhalation aerosol), PT005 (formoterol inhalation aerosol), PUR118, QMF149 (indacaterol/mometasone), QVA149 (glycopyrrolate/indacaterol inhalation), Relovair vilanterol/fluticasone furoate, RV568, TD-4208 (LAMA), tetomilast, vilanterol (long-acting beta2 agonist), Veldona interferon-alpha, and a combination thereof.

In another embodiment of the present invention, the nebulizer may be adapted for topical administration or for systemic absorption of drugs delivered for the local treatment of respiratory disease. The nebulizer is further efficient and reproducible systemic delivery is lung deposition.

In another embodiment of the present invention, the nebulizer may be used with therapeutic agents that are antiasthmatics, including bronchodilators and anti-inflammatories, particularly of steroid type, having a local therapeutic action in the lungs and/or a systemic therapeutic action after absorption in the blood.

The nebulizer of the present invention are also suitable for dispensing any medicaments which may be administered in aerosol formulations and useful in inhalation therapy e.g.; anti-allergics, e.g. cromoglycate (e.g. as the sodium salt), ketotifen or nedocromil (e.g. as sodium salt); anti-inflammatory steroids, e.g. beclomethasone (e.g. as dipropionate), fluticasone (e.g. as propionate), flunisolide, budesonide, rofleponide, mometasone (e.g as furoate), ciclesonide, triamcinolone acetonide; anticholinergics, e.g. ipratropium (e.g. as bromide), tiotropium, atropine or oxitropium and salts thereof. It will be clear to a person skilled in the art that, where appropriate, the medicaments may be used in the form of salts, (e.g. as alkali metal or amine salts or as acid addition salts) or as esters (e.g. lower alkyl esters) or as solvates (e.g. hydrates) to optimize the activity and/or stability of the medicament and/or to minimise the solubility of the medicament in the propellant.

Medicament may be used in the form of racemate or in the form of a pure isomer e.g. R-salmeterol or S-salmeterol.

In another embodiment of the present invention the nebulizer may further comprise monitoring system such as a sensor which detects and may further control the rotation of the actuating member in order to count the actuations of the nebulizer. The sensor is further adapted for breath actuating mechanism such that when the fluid, preferably a liquid, more particularly a pharmaceutical composition such as medication, is nebulized, an aerosol is formed that can be breathed in or inhaled by a user. Usually the inhaling is done at least once a day, more particularly several times a day, preferably at set intervals.

In another embodiment of the present invention, the sensor may be an air flow sensor positioned within the air-containing volume and configured to generate signals indicative of air flow generated by a patient's involuntary cough event occurring at nebulization and further a processor configured to receive signals from the air flow sensor and to evaluate the involuntary cough event. The sensor may further send a feedback signal to adjust and vary the amount of resistance to the air flow for respiratory exercise training and incentive spirometry use. Pressure sensor may further be used to indirectly measure other variables such as fluid/gas flow, speed, water level, and altitude. The pressure sensor is selected from the group consisting of gauge pressure sensor, differential pressure sensor, absolute pressure sensor, sealed pressure sensor and any combination thereof.

In another embodiment of the present invention, the monitoring elements may further count the actuations of the nebulizer by detecting any rotation of the inner part relative to the upper part of the housing. The monitoring device may further operate purely or partially mechanically.

Figures 3A, 3B:
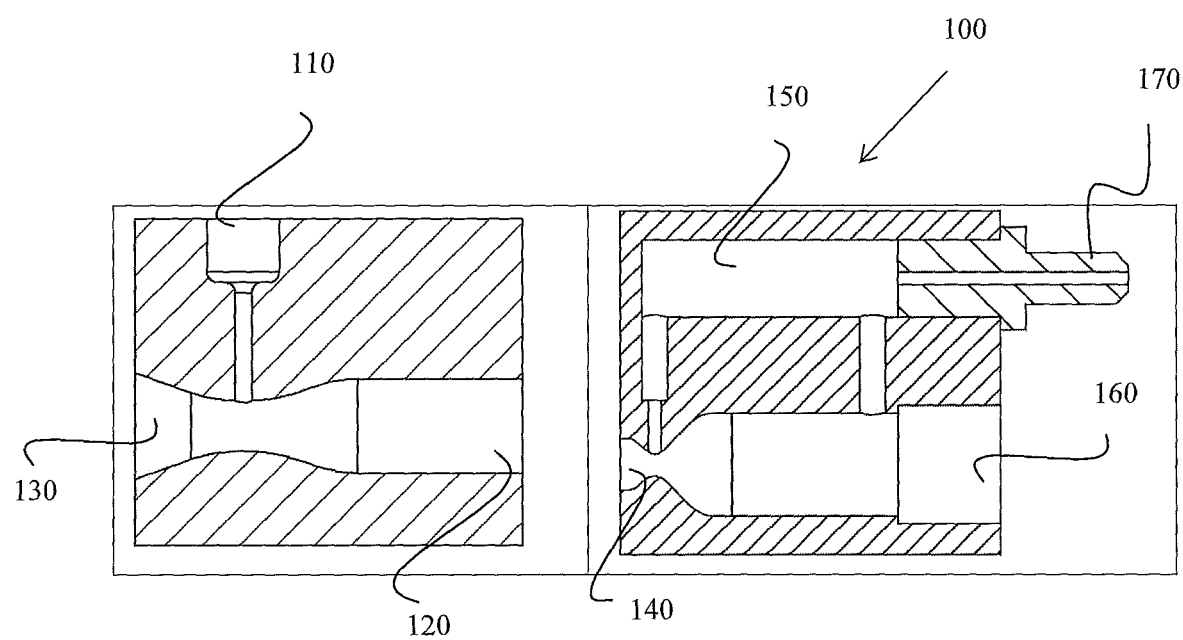
FIGS. 3A-3B present a cross section of the venturi system of the nebulizer of the present invention.

Reference is now made to FIGS. 3A-B which illustrate a nozzles system 100 of the present invention for dispensing an effective measure of a medicament in the form of a mist, comprising: a nebulizer comprising an air actuator comprising at least one inlet of liquefied gas (LG), at least one air outlet, at least one first LG-expending volume and at least one second air-containing volume, the first and second volumes are effectively separated by means of an LG-blocking member, a container with a LG source. The container is in a fluid connection with the LG-expending volume via at least one LG inlet, valve means in communication with the air actuator and at least two nozzles in fluid communication with the nebulizer's air outlet.

FIG. 3A further illustrates a classic venturi nozzles system 100 comprising an air inlet 120, a medication inlet 110 and a medication-air mixture outlet 130. The venturi nozzles system is designated for the medication rate of flow comparing to the air rate of flow and further for decrease the medication droplet size or medication particle size. The medication particle size dispersed from the nebulizer of the present invention is proportional to the air velocity due to the shear forces and surface tension balance on each droplet.

FIG. 3B further illustrates a cross section of the nebulizer of the present invention comprising venturi nozzles in a predefined arrangement. The venturi nozzle is based upon a push and pulls mechanism. The nebulizer comprises an air inlet 160 for delivering air flow, a medication inlet 170, a medication reservoir 150 and an air-medication mixture outlet 140 for delivering the fluid or medication droplets. The air inlet diameter is configured to provide a pressure difference such that the downstream pressure may further empty the inner cavity of the liquid reservoir and prevent unnecessary residuals resulting from low pressure or any fluid adherent within the nebulizer. The venturi nozzle, low pressure mixing chamber and the air-containing volume are configured such that at standard temperature and pressure (STP) a differential pressure results in no medication that is drawn upward through the primary suction line for nebulization and discharged through the nebulizer outlet until a negative inspiratory pressure is created from inhalation by the subject. Furthermore, the venturi nozzle may be horizontally oriented when in use.

It is another embodiment of the present invention, at least one nozzle is configured with a diameter of about 0.2 mm to about 0.9 mm to provide a droplets distribution of more than 70% of a medication.

It is another embodiment of the present invention, at least one nozzle is preferably with a diameter of about 0.5 mm to disperse a droplets size is in a range of about 2 µm to about 3 µm.

It is another embodiment of the present invention, at least one first nozzle is preferably with a diameter of about 0.3 mm and at least one second nozzle is with a diameter of about 0.5 mm, respectively.

Preferably, the overall cross sectional area of the nozzle outlets is 25 to 500 square micrometers.

As FIG. 3B demonstrates, the air within the air inlet flow via constricted section with a reduced diameter, the reduction in diameter causes an increase in the fluid flow speed thus the velocity of the fluid increases as the cross sectional area decreases, with the static pressure correspondingly decreasing resulting a fluid suction. Thereby, an increase in the speed of the fluid occurs simultaneously with a decrease in pressure or a decrease in the fluid's potential energy (e.g Venturi effect). Furthermore, when the fluid such as a medication, flows through the nozzle tube that narrows to a smaller diameter, the partial restriction causes a higher pressure at the inlet than that at the narrow end. This pressure difference causes the fluid to accelerate toward the low pressure narrow section, in which it thus maintains a higher speed. The direct relationship between pressure difference and fluid speeds may further allow to determine the volumetric flow rate.

In another embodiment of the present invention, in order to provide a negative pressure, thus sucking in all of the fluid, the liquid reservoir is further connected to an additional narrow tube which further configured to provide additional pressure from the back side of the liquid reservoir. The additional pressure enables and accelerates the reservoir emptying from the remained liquid droplets.

The venturi nozzles system is designated for the medication rate of flow comparing to the air rate of flow and further for decreasing the medication droplet size or medication particle size. The medication particle size dispersed from the nozzles system of the present invention is proportional to the air velocity due to the shear forces and surface tension balance on each droplet.

The formulation below demonstrates the calculation of flow rate using orifice plate calculator for incompressible flow, based on the Bernoulli principle:

$$\frac{p_1}{\rho} + \frac{v_1^2}{2} + g\,z_1 = \frac{p_2}{\rho} + \frac{v_2^2}{2} + g\,z_2 + \frac{\Delta p_{1-2}}{\rho}$$

where is:
p—pressure
ρ—density
V—velocity
g—gravitational constant (9.81 m/s2)
z—geodetic height
when assuming that the pressure lost is negligible (pressure drop is obvious and included with coefficient of discharge as introduced bellow):

$\Delta p_{1=2}=0$ and:

$gz_1 = gz_2$

When velocities substituted with flow rate:

$$V_1 = \frac{4Q}{\pi D_L^2} V_2 = \frac{4Q}{\pi D_2^2}$$

where is: Q—volumetric flow rate

D—diameter

Pressure drop through the orifice resulting from the increase of velocity which may be calculated as follows:

$$\frac{p_1 - p_2}{\rho} = \frac{1}{2}\left(\frac{16Q^2}{\pi^2 D_2^4} - \frac{16Q^2}{\pi^2 D_L^4}\right)$$

or:

$$2(p_1 - p_2) = \frac{16Q^2}{\pi^2}\left(\frac{1}{D_2^4} - \frac{1}{D_1^4}\right)$$

Expressing flow rate from the previous equation leads to:

$$Q = \sqrt{\frac{1}{1 - \left(\frac{D_2}{D_1}\right)^4}} \frac{\pi D_2^2}{4} \sqrt{\frac{2(p_1 - p_2)}{\rho}}$$

Substituting:

$$E = \sqrt{\frac{1}{1 - \left(\frac{D_2}{D_1}\right)^4}}$$

Additional values are calculated using following equations:

Mass Flow:

$$G = \rho Q$$

Velocities:

$$V_1 = \frac{4Q}{\pi D_L^2} V_2 = \frac{4Q}{\pi D_2^2}$$

Referring to Bernoulli's equation in the special case of incompressible flows, the theoretical pressure drop at the constriction is given by:

$$p_1 - p_2 = \frac{\rho}{2}(v_2^2 - v_1^2)$$

where ρ is the density of the fluid, $v_1$ is the (slower) fluid velocity where the pipe is wider, $v_2$ is the (faster) fluid velocity where the pipe is narrower (as seen in the figure). This assumes the flowing fluid (or other substance) is not significantly compressible—even though pressure varies, the density is assumed to remain approximately constant.

A venturi may be further used to measure the volumetric flow rate, Q.

Since $$Q = v_1 A_1 = v_2 A_2$$

$$p_1 - p_2 = \frac{\rho}{2}(v_2^2 - v_1^2)$$

then $$Q = A_1 \sqrt{\frac{2}{\rho} \cdot \frac{(p_1 - p_2)}{\left(\frac{A_2}{A_1}\right)^2 - 1}} = A_2 \sqrt{\frac{2}{\rho} \cdot \frac{(p_1 - p_2)}{1 - \left(\frac{A_2}{A_1}\right)^2}}$$

The nebulizer is configured to increase both (i) deposition of a medicament and (ii) kinetics per internal surface area of the alveoli to the respiratory tract by means of a dual nozzles system.

In another embodiment of the present invention, the nozzles system of the present invention may comprise at least one venturi nozzle thus, based upon venturi effect as a jet effect. The velocity of the fluid increases as the cross sectional area decreases, with the static pressure correspondingly decreasing.

In another embodiment of the present invention the nozzles system of the present invention may comprise at least one Laskin nozzle or/and swirl nozzle interconnected with a venturi nozzle in a predefined direction and angle.

In another embodiment of the present invention, the nozzles system may comprise at least two venturi nozzles interconnected in a predetermined angle (α,β) and direction such that the droplet size of a medication dispersed from the nebulizer is in a range of about 1 μm to about 5 μm. The nozzle-system further provides jets of liquid which converge at an optimized angle therefore, dispersing an effective measure of medication having an average particles size in the range of about 1 μm to about 7 μm.

In another embodiment of the present invention, the air outlet may further include an orifice having a diameter of about 0.5 mm to about 1.5 mm, operably configured to emit effective measure of the medicament having average particles size equal to or less than 5 μm. Additional or alternatively, the LG is with a pressure operably configured to emit effective measure of the medicament having average particles size equal to or less than 5 μm. Additional or alternatively, the second air-containing volume is with a volume operably configured to emit effective measure of the medicament having average particles size equal to or less than 5 μm. Additional or alternatively, the actuator is with a speed of movement operably configured to emit high medicament quantity having average particles size equal to or less than 5 μm.

Figure 4A:
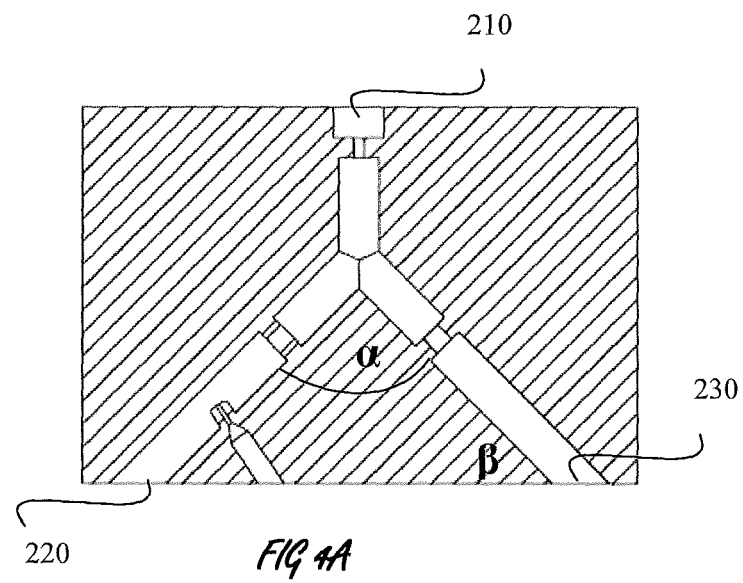
FIGS. 4A-4B illustrate a cross section of the nozzles system for dispensing a consecutively dose of a medicament in the form of a mist, of the present invention.
Figure 4B:
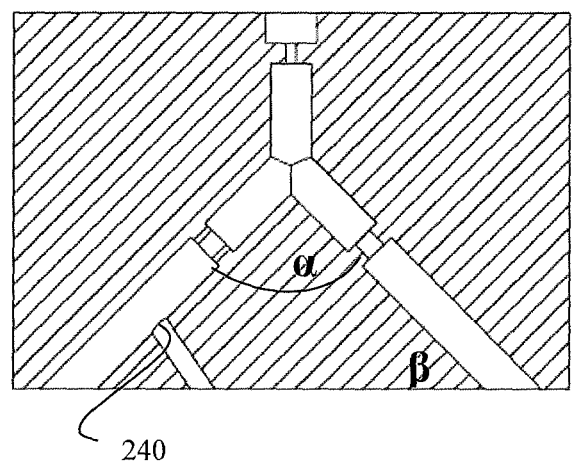
Figure 5A:
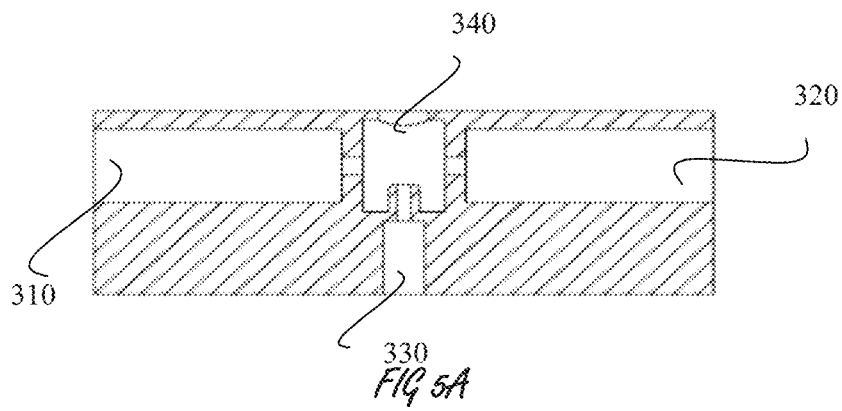
FIGS. 5A-5D illustrate a cross section of the nozzles system for dispensing a consecutively dose of a medicament in the form of a mist, of the present invention; and, FIGS. 6-19 present graphs of a medication droplets distribution of the nebulizer comprising a dual nozzle, of the present invention.
Figure 5B:
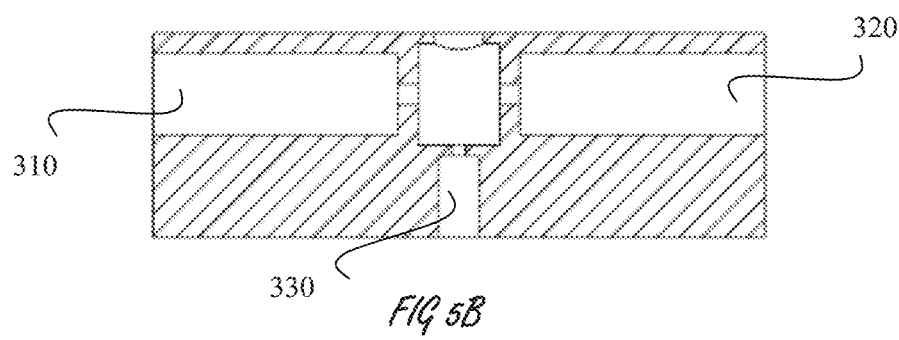
Figure 5C:
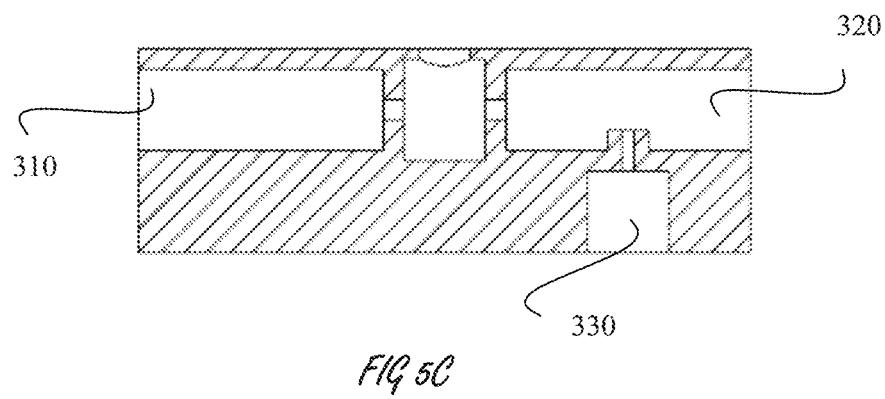
Figure 5D:
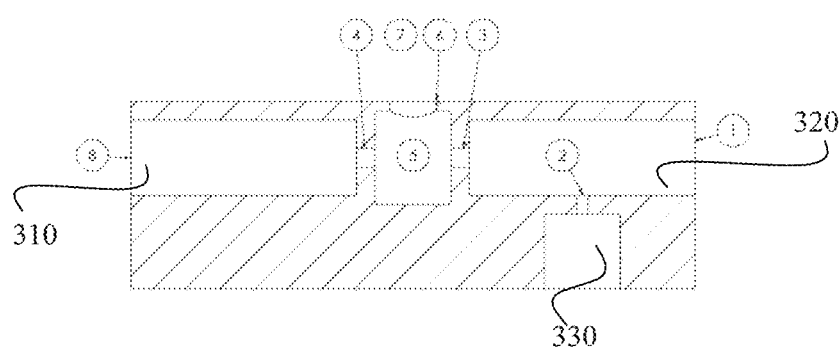
Figure 6:
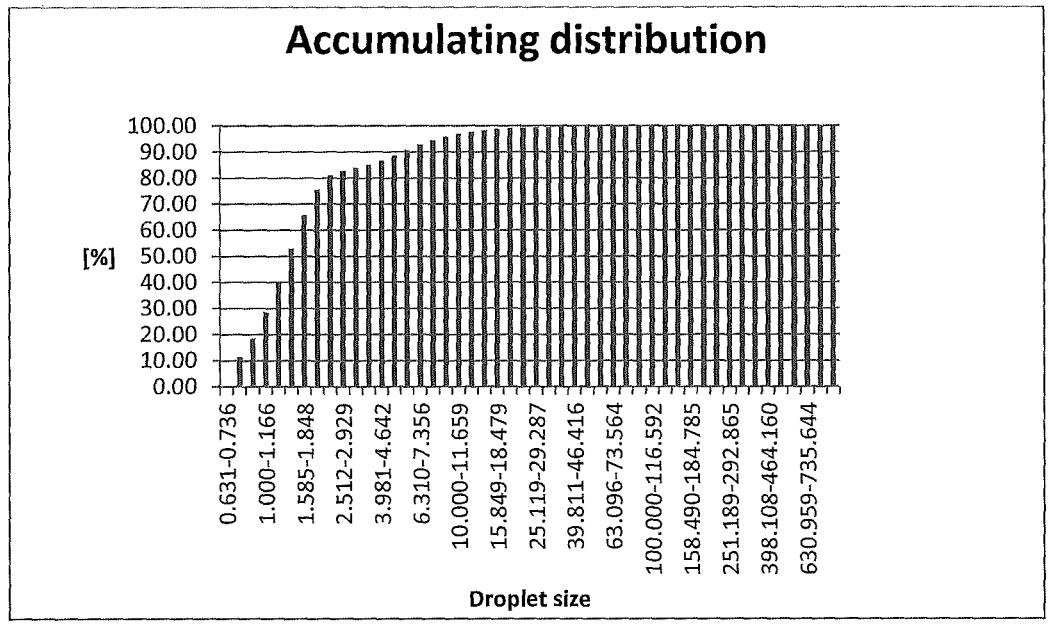
Figure 7:
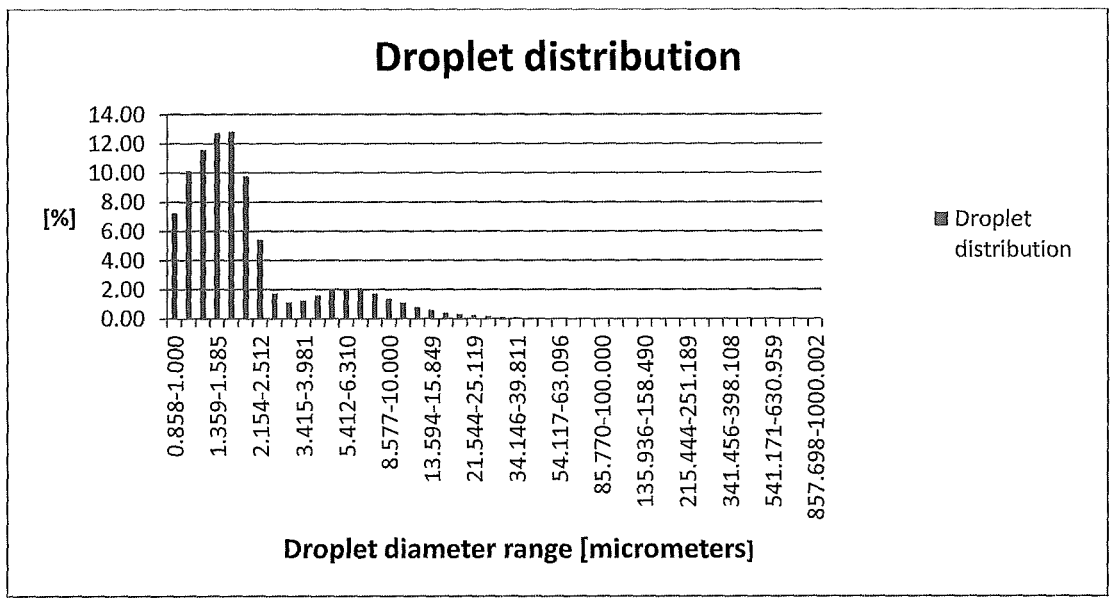
Figure 8:
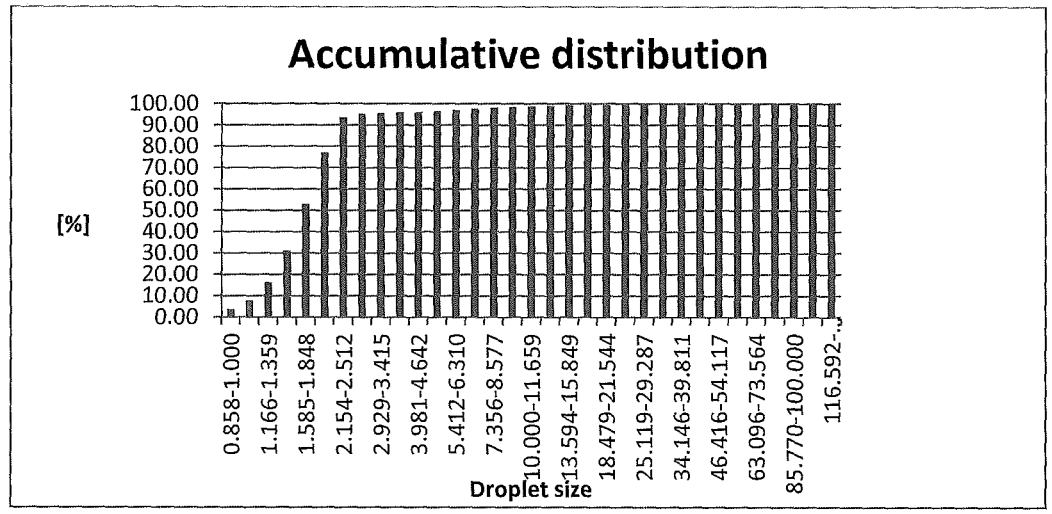
Figure 9:
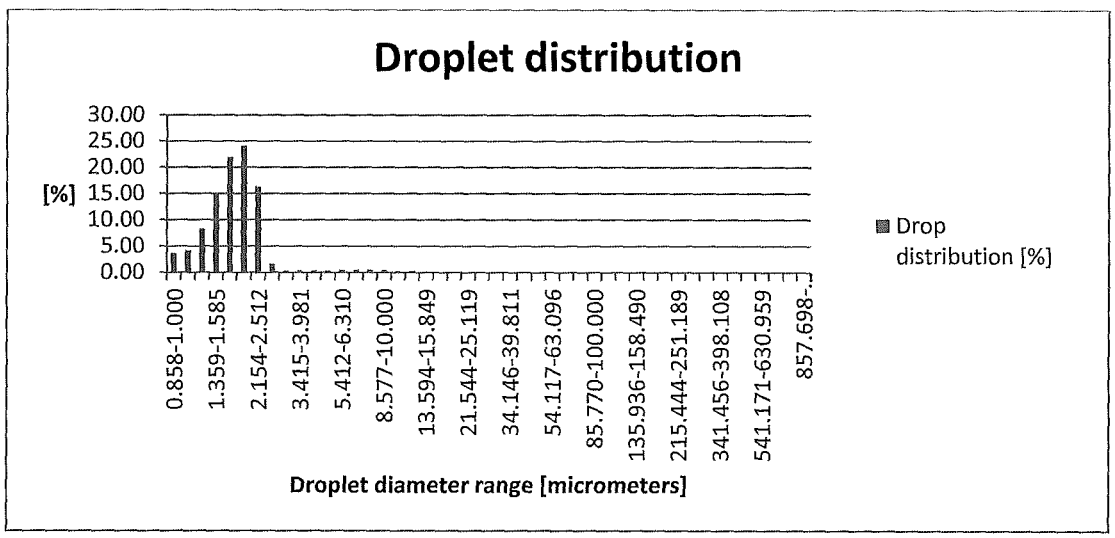
Figure 10:
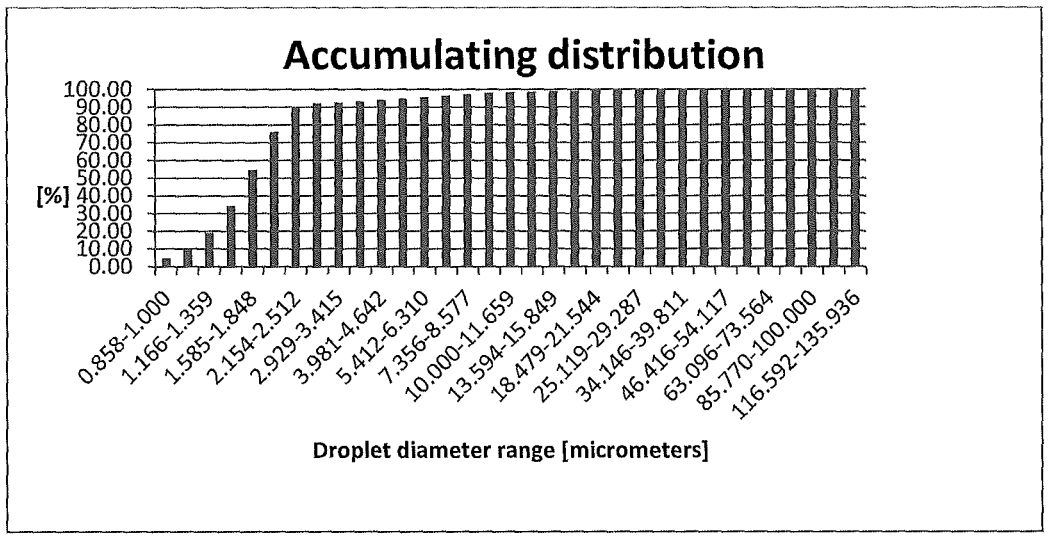
Figure 11:
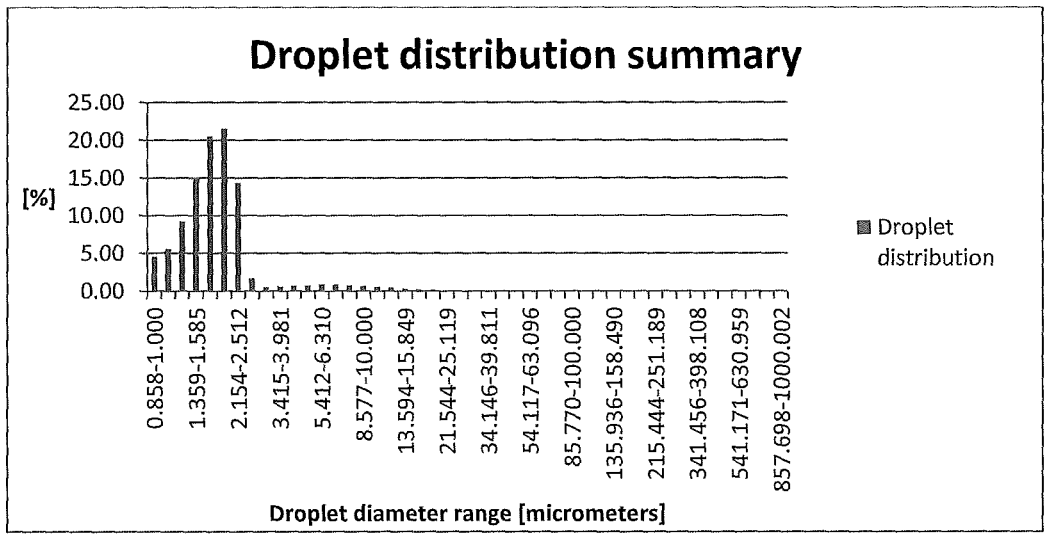
Figure 12:
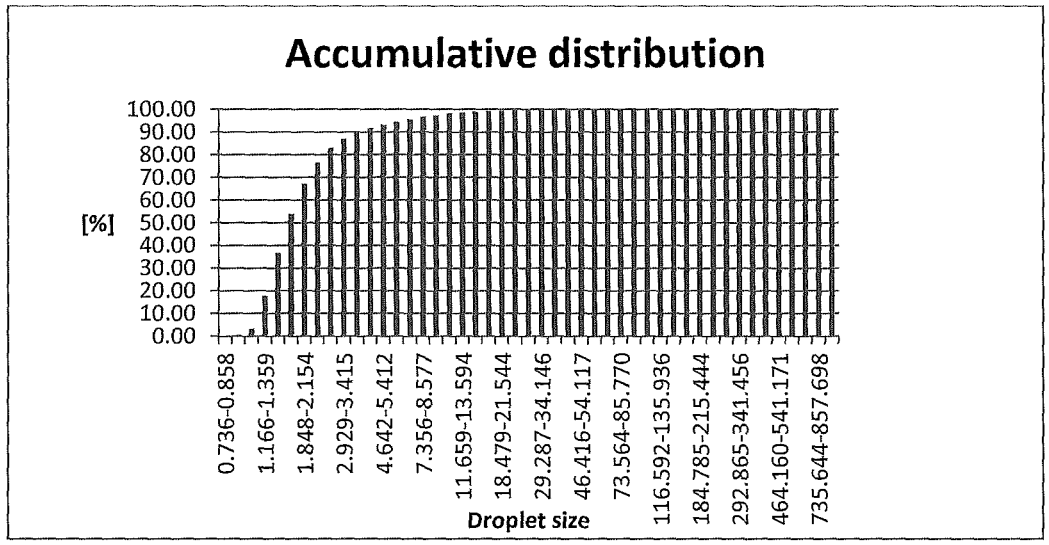
Figure 13:
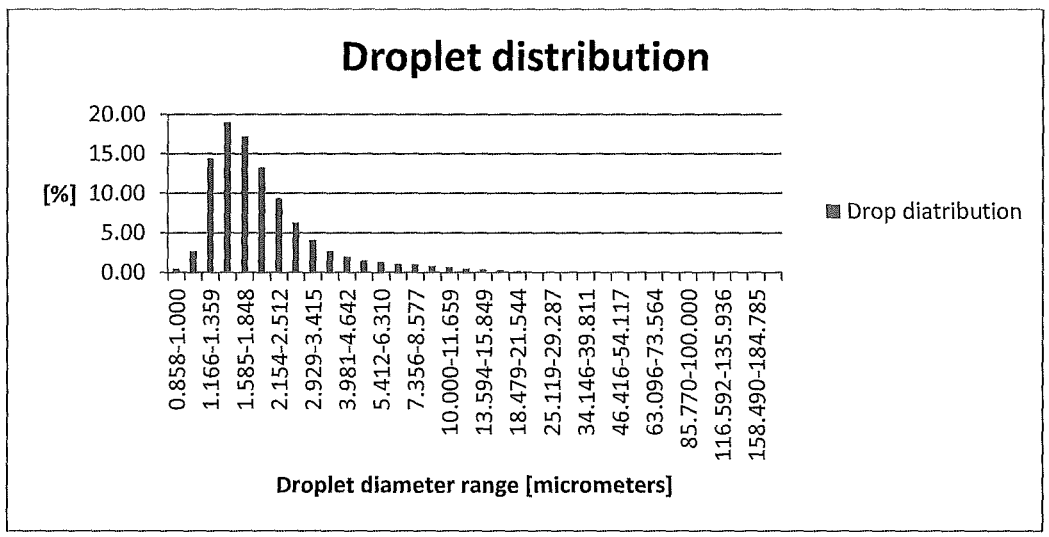
Figure 14:
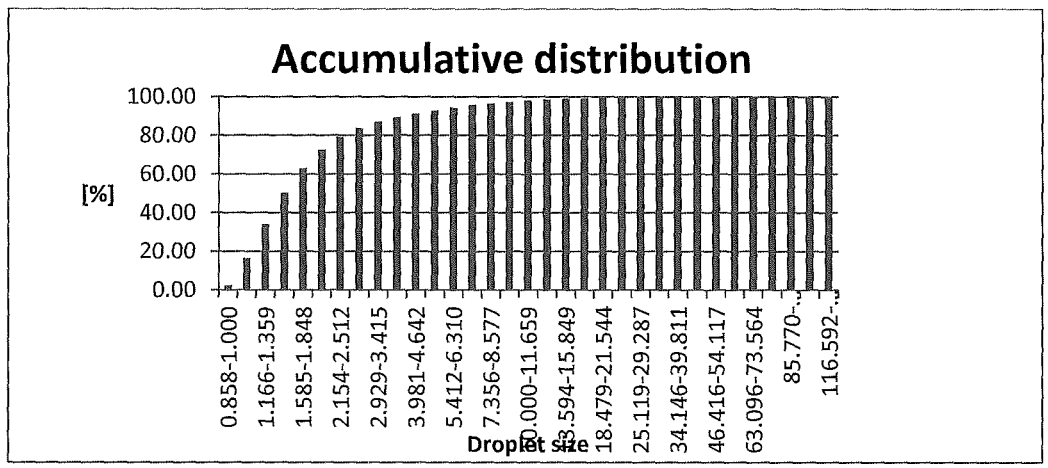
Figure 15:
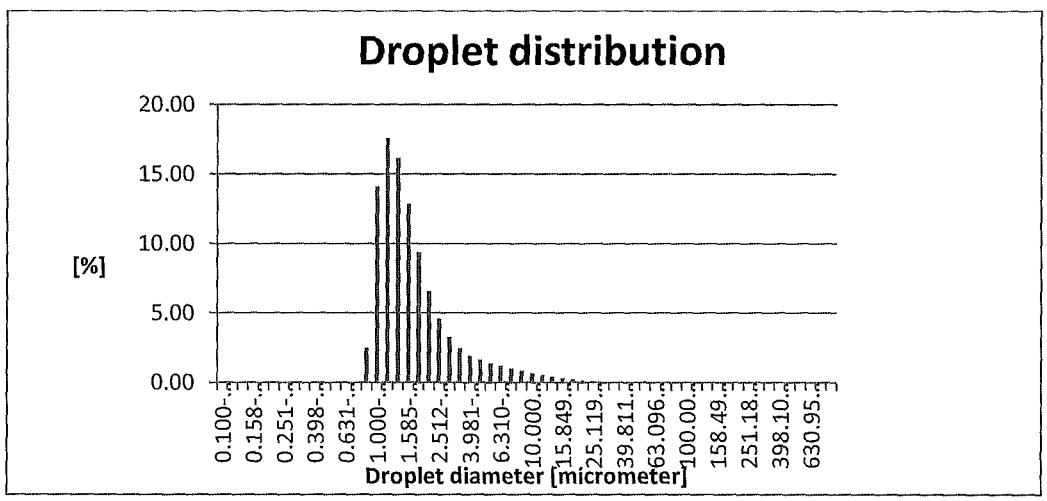

Reference is now made to FIGS. 4A-B which illustrate the nozzles system of the present invention, comprising a dual nozzle arrangement configured in a predefined angle (α, β<90° on which a primary air stream accelerates the medication flow. The nozzles system comprises a primary orifice 220, a secondary orifice 230 and further an exit orifice which designated to provide a preretirement droplet size of a medication dispersed from the nozzles system having a diameter in a range of about 1 μm to about 5 μm.

Without wishing to be bound by theory, according to the laws governing fluid dynamics, a fluid's velocity must increase as it passes through a constriction to satisfy the principle of continuity, while its pressure must decrease to satisfy the principle of conservation of mechanical energy. Thus, any gain in kinetic energy a fluid may accrue due to its increased velocity through a constriction is negated by a drop in pressure.

In the nebulizer of the present invention the medication flows through a nozzle comprising a tube that narrows to a smaller diameter thus, the partial restriction causes a higher pressure at the inlet than that at the narrow end. This pressure difference causes the medication to accelerate toward the low pressure narrow section, in which it thus maintains a higher speed. The venturi nozzles system of the present invention uses the direct relationship between pressure difference and fluid speeds to determine the volumetric flow rate of a medication and further to provide medication droplets size in the range of about 0.75 μm to 7 μm. An equation for the drop in pressure due to the Venturi effect may be derived from a combination of Bernoulli's principle and the continuity equation.

In another embodiment of the present invention, at least two nozzles are interconnected in a vertically or horizontally manner to each other.

In another embodiment of the present invention, the nebulizer meets and compliance with FDA regulations.

Reference is now made to FIGS. 5A-5D which illustrate a colliding stream nozzles system predefined arrangement. The colliding stream nozzles system comprises a first air channel 310, a second air channel 320, and a medication channel 330. When a medication is released from the medication channel 330 a mixture of air and medication is obtained within the mix channel 340 resulting a droplets size in a predefined velocity and rate. FIG. 5C further illustrates that a mixture of medication and air in a predefined velocity already obtained.

FIG. 5D illustrates a nozzle system having ports 1, 2, 3, 4, 6, 7 and 8, and channels 310, 320, 330 and 5 (or 340), as shown. The figure further illustrates the incompressible flow, based on the Bernoulli principle between port 1 to port 7:

$$\frac{P_1}{g\rho} + \frac{V_1^2}{2g} + Z_1 = \frac{P_7}{g\rho} + \frac{V_7^2}{2g} + Z_7 + \Delta H_{1-7}$$

Where:
P—pressure
ρ—density
V—velocity
g—gravitational constant (9.81 m/s2)
z—geodetic height
H—Head losses
Where:

$$V_1=0,\ Z_1=Z_2,\ P_7=0$$

$$\Delta H_{1-7} = \sum k\frac{V_7^2}{2g} + \frac{\Delta\dot{E}_{\tau 1-7}}{\dot{m}g} \approx 7\frac{V_7^2}{2g} + \frac{\Delta\dot{E}_{\tau 1-7}}{\dot{m}g}$$

$\Delta E_\tau$ = Power (energy) losses at mixing chamber $$\frac{P_1}{\rho} = 8\frac{V_7^2}{2} + \frac{\Delta\dot{E}_{\tau 1-7}}{\dot{m}}$$

The flow between port 8 and 7:

$$\frac{P_8}{g\rho} + \frac{V_8^2}{2g} + Z_8 = \frac{P_7}{g\rho} + \frac{V_7^2}{2g} + Z_7 + \Delta H_{8-7}$$

$$V_8 = 0,\ Z_8 = Z_7,\ P_7 = 0$$

$$\Delta H_{8-7} = \sum k\frac{V_7^2}{2g} + \frac{\Delta\dot{E}_{\tau 8-7}}{\dot{m}g} \approx 2\frac{V_7^2}{2g} + \frac{\Delta\dot{E}_{\tau 8-7}}{\dot{m}g}$$

$$\frac{P_8}{\rho} = 3\frac{V_7^2}{2} + \frac{\Delta\dot{E}_{\tau 8-7}}{\dot{m}}$$

The sum of energy losses is the energy required to refraction of the liquid into small droplets.

$$\dot{E}_{sum}=\Delta\dot{E}_{\tau 1-7}\Delta\dot{E}_{\tau 8-7}$$

Continuity Equation:

$$\dot{m}_{G8} + \dot{m}_{G1} + \dot{m}_L = \rho_{GL} \times V_7 \times \pi \times \frac{D_6^2}{4}$$

$\rho_{GL}$—average density of Gas and liquid $$\dot{m}_{G1} + \dot{m}_L = \rho_{GL} \times V_2 \times \pi \times \frac{D_2^2}{4}$$

$$\dot{m}_{G1} + \dot{m}_L = \rho_{GL} \times V_3 \times \pi \times \frac{D_3^2}{4}$$

$$\dot{m}_{G8} = \rho_G \times V_4 \times \pi \times \frac{D_4^2}{4}$$

Examples $$P_1=P_8=4\text{ bar}$$

$$m_{G8}\dot{}+m_{G1}\dot{}=1.2\times10^{-4}\text{ kg/s}$$

Symmetric Distribution $$m_{G8}\dot{}=m_{G1}\dot{}=0.6\times10^{-4}\text{ kg/s}$$

$$m_L\dot{}=2.7\times10^{-5}\text{ kg/s}$$

$$D_6=4\text{ mm}, D_1=D_8=2.5\text{ mm},$$

From Continuity Equation:

$$\dot{m}_{G8} + \dot{m}_{G1} + \dot{m}_L = \rho_{GL} \times V_7 \times \pi \times \frac{D_6^2}{4}$$

The average density is function of the volume, therefore:

$$\rho_{GL}=1.47\text{ kg/m}^3$$

Can get $V_7 \approx 8$ m/s

And $\dot{E}_{sum} \approx 34$ W

As demonstrates above the droplets size is controlled and changed resulting from the different diameters thereby different velocities. Table 2 below demonstrated the diameter of ports 2, 3 and 4, the droplets velocity and droplets size derived.

TABLE 2

|   | $D_2$ (mm) | $V_2$ (m/s) | $D_3$ (mm) | $D_4$ (mm) | $V_3$ (m/s) | $V_4$ (m/s) | Diameter of droplets (μm) |
|---|---|---|---|---|---|---|---|
| I | 1.0 | 75 | 0.5 | 0.5 | 254 | 254 | 2 |
| II | 1.0 | 75 | 0.6 | 0.6 | 176 | 176 | 4 |
| III | 1.0 | 75 | 0.8 | 0.8 | 99 | 99 | 6 |

The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

Reference is now made to FIGS. 6 to 19 which illustrate graphs of droplets distribution which determine the quality of the mist sprayed out of the present invention's custom designed nozzles system.

Figure 16:
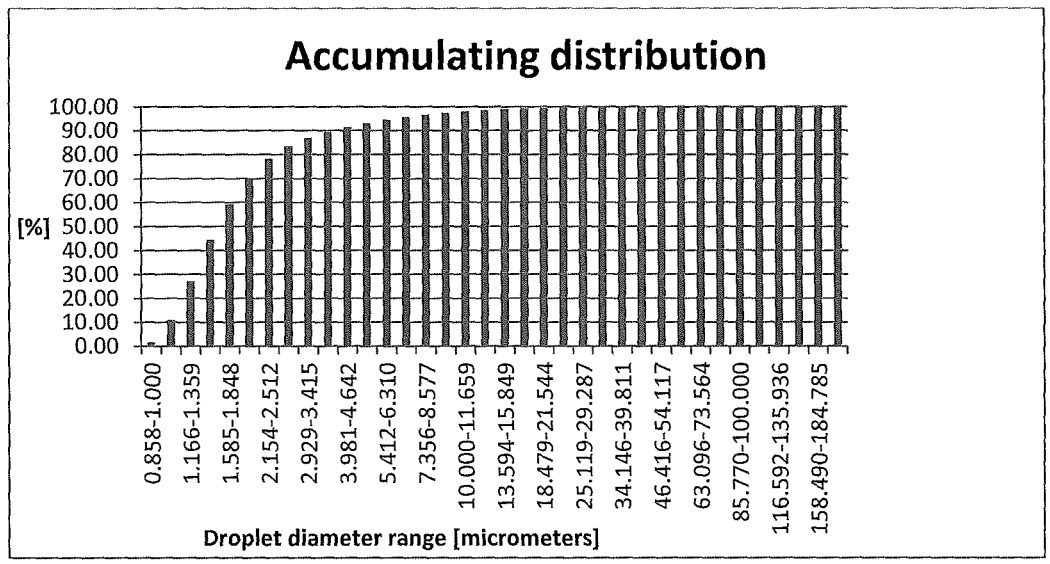
Figure 17:
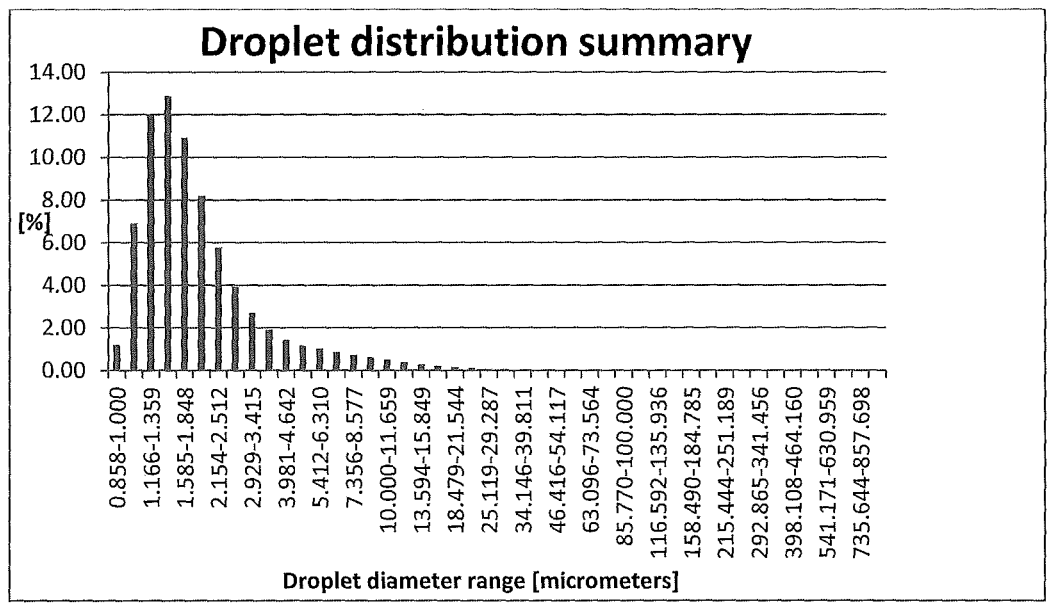
Figure 18:
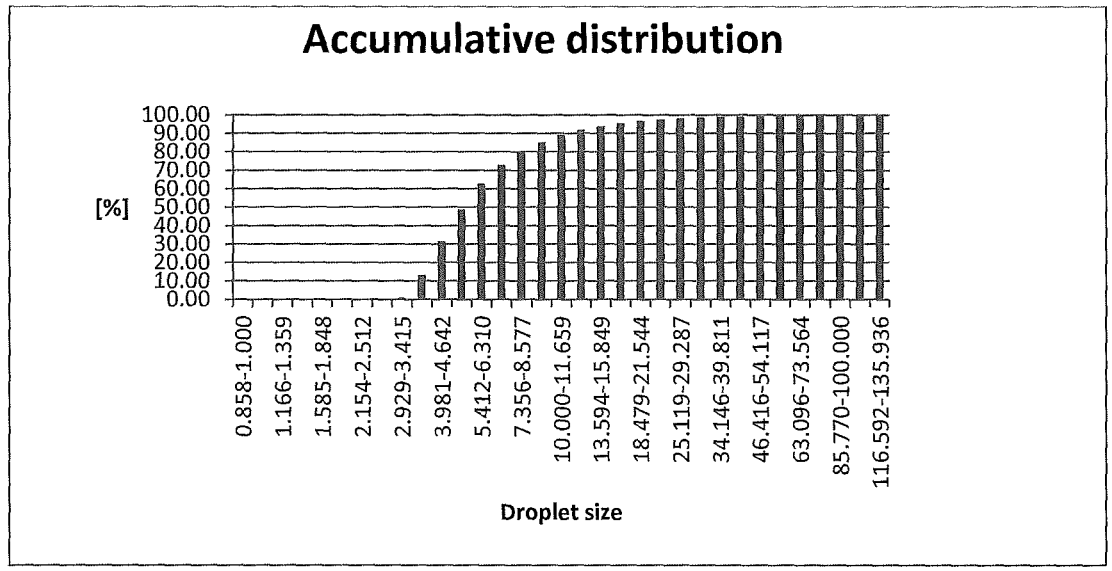
Figure 19:
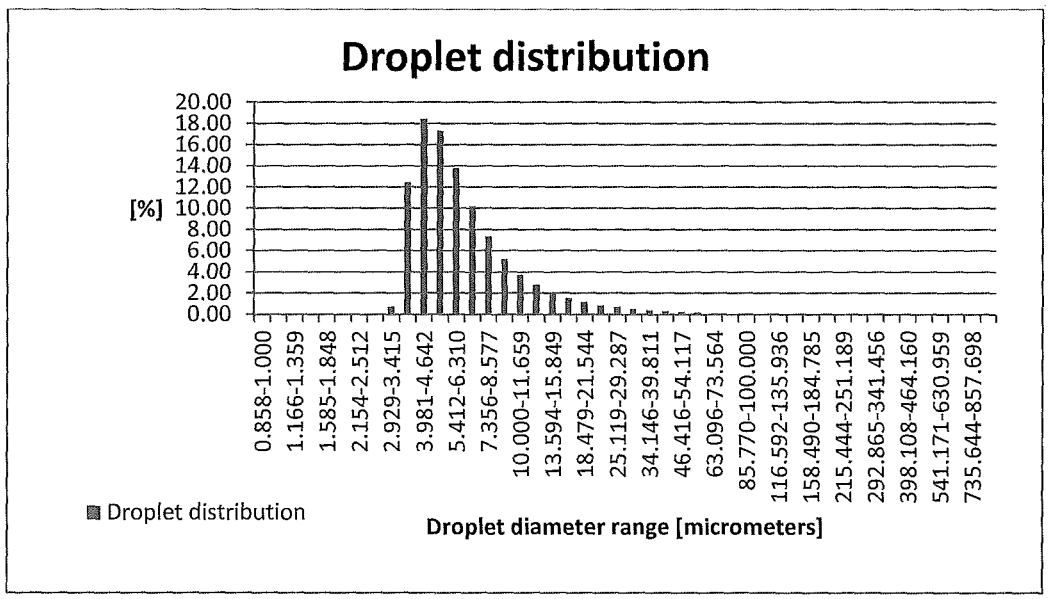

FIG. 16 further demonstrates a Gaussian curve of the droplets diameter of a medication dispersed from the nebulizer comprising the nozzles system of the present invention vs. the particles percentage amount. As illustrated, the nebulizer may provide more that 50% droplets from the medication droplets population having a 2 μm diameter. Furthermore, the nebulizer may further provide more than 75% droplets from the medication droplets population having a 3 μm diameter. The graph is characterized by a bell-shaped curve of the diffusion of medication particles which further illustrates that an optimal absorption percentage of medication can be achieved in droplets size in the range of about 0.8 μm to about 6 μm.

The nebulizer was further tested using the MALVERN Spray tech particle sizing analyzer for determining the droplets diameter and duration vs. the medication dispersed dose.

Table 3 below demonstrates the particle size and distribution when using the nebulizer of the present invention. The nebulizer of the present invention is with ability to generate a mist that consists of 80% droplets smaller than 3 microns and 90% droplets smaller than 5 microns.

TABLE 3

| CRITERIA\ NOZZLE EXP | Peak particle size [μm] | Accumulated distribution >75% range [μm] | Accumulated distribution >80% range [μm] |
|---|---|---|---|
| 1_3.5b_27mms_C | ~1.8 | 1.848-2.154 | 2.154-2.512 |
| 1_3.5b_27mms_D | ~2.0 | 1.848-2.154 | 2.154-2.512 |
| Summary 3.5bar | ~2.0 | 1.848-2.154 | 2.154-2.512 |
| 1_4b_27mms_3 | ~1.5 | 2.154-2.512 | 2.512-2.929 |
| 1_4b_27mms_4 | ~1.4 | 2.154-2.512 | 2.512-2.929 |
| Summary 4 bar | ~1.5 | 2.154-2.512 | 2.512-2.929 |
| DBL_3.2B_1 | ~4.3 | 7.356-8.577 | 7.356-8.577 | the present invention further provides a nebulizer for improving medicament's alveolar deposition is with a medication lunching velocity of about 40 μL/s, air velocity of about 100 cc/s, whilst the minimum diameter of the tube of the venturi system is of about 0.95 mm and the minimum diameter of the medication inlet is of about 0.38 mm. This results an air-medication mixture having a velocity of about 20 m/s. The nebulizer further provides droplets with an average diameter of about 2.4 μm.

In another embodiment of the present invention, the nebulizer may further be adapted for systemic administration of active compounds and drug compositions (e.g via a route of administration of medication nutrition or other substance into the circulatory system so that the entire respiratory system is affected), therefore, adapting the pulmonary rout or the respiratory system as a port of entry for systemic distribution and/or absorption of drugs (e.g. insulin) via enteral administration.

The invention claimed is:

1. A nebulizer for consecutively dispensing one or more doses of a medicament in the form of a mist, comprising:
    a. an energy source (ES) comprising one or more of the following: electric motor, electric linear actuator, electromagnetic solenoid based actuator, spring operated mechanism, hydraulic pump, compressed gas (CG), flywheel, steam engine, carnot machine, stirling cycle;
    b. an air-containing volume;
    c. an air outlet fluidly connected to said air-containing volume; and
    d. an air actuator in communication with at least two valve means, said air actuator being adapted to release a flow of compressed air from the air-containing volume through said air outlet by application of force from the energy source at such time as a predetermined pressure has been reached in said air-containing volume;
    e. a nozzle system comprising a nozzle air inlet being in fluid communication with said air outlet to receive said flow of compressed air, an air-mixture outlet and a medication inlet, the nozzle system being configured to mix between said flow of compressed air and a medication in a liquid form, wherein said nozzle system comprises at least two nozzles being in fluid communication with said air outlet, wherein that at least two nozzles are of at least one of the following types: venturi nozzle, laskin nozzle, annular flow high velocity, colliding streams nozzle, additive energy nozzles, and swirl nozzle; and
    f. a medication container adapted to contain the medication in the liquid form and being in communication with said medication inlet;
    wherein dimensions of said air-containing volume said air outlet, said nozzle air inlet, said medication inlet, and said air-mixture outlet are selected to provide said compressed air being released into said nozzle system at a predetermined pressure in said air-containing volume of about 20 psig to about 100 psig, said mist comprises a distribution of the medication with droplet size between 1 μm to 7 μm being released in quick succession.

2. The nebulizer system according to claim 1, having at least one of the following configurations: (a) said valve means is configured to control the actuation of said air actuator; (b) said valve means comprises at least one control valve having an idle state and an automatic state and at least two directing valves that are based on ferromagnetic mechanism; and (c) said valve means comprises an energy source valve in a fluid connection with said energy source being configured to control movement of said air actuator.

3. The nebulizer system according to claim 1, wherein said droplets are released in a quick succession form at a rate of about 2.5 ml droplets of said medication per 2 minutes.

4. The nebulizer according to claim 1, wherein said air actuator has at least one of the following configurations: (a) said air actuator is partially composed of ferromagnetic material; and (b) said air actuator comprises at least one of the following: a piston pump, a turbine, a rotor, and an inflatable membrane spring.

5. The nebulizer according to claim 1, additionally comprising an air inlet for inserting air into said air-containing volume.

6. The nebulizer according to claim 1, wherein said at least two nozzles are interconnected in an angle α<90°.

7. The nebulizer according to claim 1, additionally comprising a metering valve in fluid connection with said medicament chamber.

8. The nebulizer according to claim 1, configured to be activated manually, semi manually or electrically.

9. The nebulizer according to claim 1, additionally comprising at least one of the following: (a) a breath actuation means configured to respond to inhalation by a subject when the subject's inhalation is sensed; and (b) spring means in communication with said air actuator, said spring means comprising at least one of mechanical spring, gas loaded spring, and gas pressure.

10. The nebulizer according to claim 1, further comprising a breath actuation means configured to sense negative pressure of subject's inhalation and configured to trigger or initiate high pressure gas flow when said negative pressure is sensed, wherein said breath actuation means comprises at least one of a pressure sensor, and Intake Air Temperature (IAT) sensor.

11. A nebulizer for consecutively dispensing a one or more doses of a medicament in the form of a mist, comprising:
   i. an energy source (ES) comprising at least one of the following: liquified gas (LG) source, electric motor, electric linear actuator, electromagnetic solenoid based actuator, spring operated mechanism, hydraulic pump, compressed gas (CG), flywheel, steam engine, carnot machine, and stirling cycle;
   ii. an air-containing volume;
   iii. an air outlet fluidly connected to said air-containing volume;
   iv. an air actuator in communication with at least two valve means, said air actuator being adapted to release a flow of compressed air from the air-containing volume through said air outlet by application of force from the energy source at such time as a predetermined pressure has been reached in said air containing volume; and
   v. a nozzle system fluidly connected to said air outlet to receive said flow of compressed air and being adapted to provide a predetermined distribution of the medicament mist dispensed from the nebulizer; wherein said nozzle system comprises a medication inlet, and a dual nozzle arrangement comprising first and second nozzles interconnected with a predetermined angle (α) and direction and being configured to provide first and second colliding streams creating said medicament mist, wherein said first stream is an air stream flowing in said first nozzle and said second stream flowing in said second nozzle is either an air stream wherein said medication inlet is located at the intersection between the first and second nozzles, or a mist stream wherein said medication inlet is in fluid communication with the second nozzle.

12. The nebulizer according to claim 11, wherein said nozzle system has at least one of the following configurations:
   a) the nozzles are venturi nozzles arranged such that the droplet size of a medication dispersed from said nebulizer is in a range of about 1 μm to about 7 μm;
   b) the nozzles are configured to disperse at least 2.5 ml of said medication in approximately 2 minutes;
   c) the nozzles are interconnected in a vertically or horizontally manner to each other;
   d) the nozzles are of a nozzle type comprising at least one of laskin nozzle, annular flow high velocity, colliding streams nozzle, additive energy nozzles, swirl nozzle;
   e) the nozzles are configured with a diameter of about 0.2 mm to about 0.9 mm configured to disperse a droplets size less than 5 μm;
   f) at least one of said nozzles is configured with a diameter of about 0.5 mm to provide a droplets distribution of more than 70% of said medication;
   g) at least one of said nozzles is configured with a diameter of about 0.5 mm to disperse a droplets size is in a range of about 2 μm to about 3 μm;
   h) the nozzles are interconnected in a vertical angle and generate a mist of about 80% droplets smaller than 3 μm;
   i) the nozzles are interconnected in a vertical angle and generate a mist of about 90% droplets smaller than 5 μm.

13. The nebulizer according to claim 11, wherein said energy source comprises the LG source, the nebulizer further comprising an LG outlet and an LG-containing volume fluidly connected to the LG source and being adapted to contain LG.

14. The nebulizer according to claim 13, wherein said air actuator separates said LG-containing volume from said air-containing volume; said air actuator is configured to allow the expansion of said LG in said LG-containing volume from its condensed liquid phase to its expanded gas phase.

* * * * *